United States Patent
Stamm et al.

(10) Patent No.: US 9,567,585 B2
(45) Date of Patent: Feb. 14, 2017

(54) ANTISENSE OLIGONUCLEOTIDE MODULATORS OF SEROTONIN RECEPTOR 2C AND USES THEREOF

(71) Applicants: Shire Human Genetic Therapies, Inc., Lexington, MA (US); University of Kentucky, Lexington, KY (US)

(72) Inventors: Stefan Stamm, Lexington, KY (US); Manli Shen, Lexington, KY (US); Serene Josiah, Cambridge, MA (US)

(73) Assignees: Shire Human Genetic Therapies, Inc., Lexington, MA (US); University of Kentucky, Lexington, KY (US)

( * ) Notice: Subject to any disclaimer, the term of this patent is extended or adjusted under 35 U.S.C. 154(b) by 0 days.

(21) Appl. No.: 14/357,388

(22) PCT Filed: Nov. 9, 2012

(86) PCT No.: PCT/US2012/064319
§ 371 (c)(1),
(2) Date: May 9, 2014

(87) PCT Pub. No.: WO2013/071022
PCT Pub. Date: May 16, 2013

(65) Prior Publication Data
US 2014/0275222 A1    Sep. 18, 2014

Related U.S. Application Data

(60) Provisional application No. 61/707,592, filed on Sep. 28, 2012, provisional application No. 61/558,407, filed on Nov. 10, 2011.

(51) Int. Cl.
*C12N 15/11* (2006.01)
*C12N 15/113* (2010.01)

(52) U.S. Cl.
CPC ....... *C12N 15/1138* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3521* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 6,333,172 B1 | 12/2001 | Rine et al. | |
| 6,432,640 B1* | 8/2002 | Polyak et al. | 435/6.13 |
| 2004/0241651 A1* | 12/2004 | Olek et al. | 435/6 |
| 2005/0246794 A1* | 11/2005 | Khvorova | A61K 31/713 800/286 |
| 2005/0255487 A1* | 11/2005 | Khvorova | A61K 31/713 435/6.11 |
| 2008/0021202 A1* | 1/2008 | Luo et al. | 530/387.3 |
| 2008/0113351 A1 | 5/2008 | Naito et al. | |
| 2009/0297485 A1* | 12/2009 | Mishra | 424/93.7 |

FOREIGN PATENT DOCUMENTS

| WO | WO 0212263 A1 * | 2/2002 |
| WO | WO 2007/106407 A2 | 9/2007 |
| WO | WO-2010/083338 A2 | 7/2010 |
| WO | WO-2010/120820 A1 | 10/2010 |

OTHER PUBLICATIONS

International Search Report for PCT/US2012/064319, 4 pages (Feb. 12, 2013).
Khanna, A. and Stamm, S., Regulation of alternative splicing by short non-coding nuclear RNAs, RNA Biology, 7(4):480-485 (2010).
Kishore, S. and Stamm, S., The snoRNA HBII-52 Regulates Alternative Splicing of the Serotonin Receptor 2C, Science Magazine, 311(5758):230-232 (2006).
Wang, Q. et al., Altered G Protein-Coupling Functions of RNA Editing Isoform and Splicing Variant Serotonin$_{2C}$ Receptors, Journal of Neurochemistry, 74(3):1290-1300 (2000).
Written Opinion for PCT/US2012/64319, 5 pages (Feb. 12, 2013).
Kishore, S. and Stamm, S., Regulation of alternative splicing by snoRNAs, Cold Spring Harbor Symposia on Quantitative Biology, LXXI: 329-334 (2006), Retrieved from the Internet: URL: http://symposium.cshlp.orgjcontent/71/329.full.pdf [retrieved on May 26, 2015].
Kishore, S. and Stamm, S., Supporting online material for the snoRNA HBII-52 Regulates Alternative Splicing of the Serotonin Receptor 2C, Science (2005), American Association for the Advancement of Science, US, Retrieved from the Internet: URL: http://www.sciencemag.orgjcontent/311/5758/230jsuppl/DC1 [retrieved on May 26, 2015].
Kishore, S. and Stamm, S., The snoRNA HBII-52 regulates alternative splicing of the serotonin receptor 2C, Science, 311(5758): 230-232 (2006).

* cited by examiner

*Primary Examiner* — Kate Poliakova-Georgantas
(74) *Attorney, Agent, or Firm* — Proskauer Rose LLP; Fangli Chen

(57) ABSTRACT

The present invention provides, among other things, oligonucleotide modulators of human 5'-HT2C receptor (HTR2C) and improved methods and composition for treating HTR2C-related diseases, disorders or conditions based on such modulators. In particular, oligonucleotides modulators according to the invention target specific regions in the Exon V/Intron V junction of the human HTR2C pre-mRNA and drive expression of HTR2C Vb splice isoform, leading to increased generation of non-edited strong HTR2C receptor and enhanced serotonin receptor activity.

19 Claims, 14 Drawing Sheets

Arrow: cannula position
VMH: ventromedial hypothalamic nucleus
Arc: arcuate nucleus of hypothalamus
3V: the third ventricle Dots: cell nuclei Uptake of the Cy3 labeled oligo after
1) Canulae implantation on day 1
2) Injection day 2 (1 μg)
3) Sacrifice after 18 hrs
4) No seizures etc observed, n=6

SEQUENCE LISTING

<160> NUMBER OF SEQ ID NOS: 28

<210> SEQ ID NO 1
<211> LENGTH: 36
<212> TYPE: RNA
<213> ORGANISM: Homo sapiens

<400> SEQUENCE: 1
uuggccauaa gaauugcagc ggcuaugcuc aauacu                               36

<210> SEQ ID NO 2
<211> LENGTH: 295
<212> TYPE: DNA
<213> ORGANISM: Homo sapiens

<400> SEQUENCE: 2
attatgtctg ccactacct agatatttgt gccccgtctg gatttcttta gatgttttat      60
tttcaacagc gtccatcatg cacctctgcg ctatatcgct ggatcggtat gtagcaatac    120
gtaatcctat tgagcatagc cgtttcaatt cgcggactaa ggccatcatg aagattgcta    180
ttgtttgggc aatttctata ggtaaataaa acttttttggc cataagaatt gcagcggcta  240
tgctcaatac tttcggatta tgtactgtga acaacgtaca gacgtcgact ggtaa         295

<210> SEQ ID NO 3
<211> LENGTH: 290
<212> TYPE: DNA
<213> ORGANISM: Homo sapiens

<400> SEQUENCE: 3
attatgtctg cctttacct agatatttgt gccccgtctg gatttcacta gatgtgctat     60
tttcaactgc gtccatcatg cacctctgcg ccatatcgct ggaccggtat gtagcaatac   120
gtaatcctat tgagcatagc cggttcaatt cgcggactaa ggccatcatg aagattgcca   180
tcgtttgggc aatatcaata ggtaattata cctggccata gaattgcagc ggctatgctc   240
aataccttcg gattatgtac tgtgaacaac ctacagacgt cgactggtaa              290

<210> SEQ ID NO 4
<211> LENGTH: 18
<212> TYPE: RNA
<213> ORGANISM: Homo sapiens

<400> SEQUENCE: 4
cauagccgcu gcaauucu                                                  18

<210> SEQ ID NO 5
<211> LENGTH: 18
<212> TYPE: RNA
<213> ORGANISM: Homo sapiens

<400> SEQUENCE: 5
aguauugagc auagccgc                                                  18

<210> SEQ ID NO 6
<211> LENGTH: 12
<212> TYPE: RNA
<213> ORGANISM: Homo sapiens

<400> SEQUENCE: 6
aguauugagc au                                                        12

```
<210> SEQ ID NO 7
<211> LENGTH: 12
<212> TYPE: RNA
<213> ORGANISM: Homo sapiens

<400> SEQUENCE: 7
gagcauagcc gc                                                          12

<210> SEQ ID NO 8
<211> LENGTH: 18
<212> TYPE: RNA
<213> ORGANISM: Homo sapiens

<400> SEQUENCE: 8
ugcaauucuu auggccaa                                                    18

<210> SEQ ID NO 9
<211> LENGTH: 36
<212> TYPE: RNA
<213> ORGANISM: Homo sapiens

<400> SEQUENCE: 9
aguauugagc auagccgcug caauucuuau ggccaa                                36

<210> SEQ ID NO 10
<211> LENGTH: 18
<212> TYPE: RNA
<213> ORGANISM: Homo sapiens

<400> SEQUENCE: 10
uagcaaucuu caugaugg                                                    18

<210> SEQ ID NO 11
<211> LENGTH: 18
<212> TYPE: RNA
<213> ORGANISM: Homo sapiens

<400> SEQUENCE: 11
uuaguccgcg aauugaaa                                                    18

<210> SEQ ID NO 12
<211> LENGTH: 18
<212> TYPE: RNA
<213> ORGANISM: Homo sapiens

<400> SEQUENCE: 12
augcucaaua ggauuacg                                                    18

<210> SEQ ID NO 13
<211> LENGTH: 18
<212> TYPE: RNA
<213> ORGANISM: Homo sapiens

<400> SEQUENCE: 13
agaaauugcc caaacaau                                                    18

<210> SEQ ID NO 14
<211> LENGTH: 18
<212> TYPE: RNA
<213> ORGANISM: Homo sapiens

<400> SEQUENCE: 14
aaaguuuuau uuaccuau                                                    18
```

```
<210> SEQ ID NO 15
<211> LENGTH: 36
<212> TYPE: RNA
<213> ORGANISM: Homo sapiens

<400> SEQUENCE: 15
aguauugagc auagccgcug caauucuuau ggccaa                                    36

<210> SEQ ID NO 16
<211> LENGTH: 10
<212> TYPE: RNA
<213> ORGANISM: Homo sapiens

<400> SEQUENCE: 16
gcauagccgc                                                                 10

<210> SEQ ID NO 17
<211> LENGTH: 195
<212> TYPE: RNA
<213> ORGANISM: Homo sapiens

<400> SEQUENCE: 17
ggaucgguau guagcaauac guaauccuau ugagcauagc cguuucaauu cgcggacuaa          60
ggccaucaug aagauugcua uuguuugggc aauucuaua gguaaauaaa acuuuuggc           120 cauaagaauu gcagcggcua ugcucaauac uuucggauua uguacuguga acaacguaca         180
gacgucgacu gguaa                                                         195

<210> SEQ ID NO 18
<211> LENGTH: 195
<212> TYPE: RNA
<213> ORGANISM: Macaca mulatta

<400> SEQUENCE: 18
ggaucgguau guagcaauac guaauccuau ugagcauagc cguuucaauu cgcggacuaa          60
ggccaucaug aagauugcua uuguuugggc aauucuaua gguaaauaaa acuuuuggc           120 cguaagaauu gcagcggcua ugcucaauac uuucggauua uguacuguga acaacguaca         180
gacgucgacu gguaa                                                         195

<210> SEQ ID NO 19
<211> LENGTH: 195
<212> TYPE: RNA
<213> ORGANISM: Pan troglodytes

<400> SEQUENCE: 19
ggaucgguau guagcaauac guaauccuau ugagcauagc cguuucaauu cgcggacuaa          60
ggccaucaug aagauugcua uuguuugggc aauucuaua gguaaauaaa acuuuuggc           120 cauaagaauu gcagcggcua ugcucaauac uuucggauua uguacuguga acaacguaca         180
gacgucgacu gguaa                                                         195

<210> SEQ ID NO 20
<211> LENGTH: 194
<212> TYPE: RNA
<213> ORGANISM: Canis familiaris

<400> SEQUENCE: 20
ggaucgguau guagcaauac guaauccuau ugagcauagc cguuucaauu cgcggacuaa          60
ggccaucaug aagauugcua uuguuugggc aauucgauau gguaaauaac guucuuggcc        120
```

```
auuagaauug cagcggcuau gcucaauacu uucggauuau guacugugaa caacguacag    180
acgucgacug guaa                                                      194

<210> SEQ ID NO 21
<211> LENGTH: 194
<212> TYPE: RNA
<213> ORGANISM: Sus scrofa

<400> SEQUENCE: 21
ggaucgguau guagcaauac guaauccuau ugagcauagc cguuucaauu cacggacuaa    60
ggccaucaug aagauugcua uuguuugggc aauuucuuua gguaaugaac uuucuuggcc    120
aguagaauug cagcggcuau gcucaauacu uucggauuau guacugugaa caacguacag    180
acgucgacug guaa                                                      194

<210> SEQ ID NO 22
<211> LENGTH: 194
<212> TYPE: RNA
<213> ORGANISM: Bos taurus

<400> SEQUENCE: 22
ggaucgguau guagcaauac guaauccuau ugagcauagc cguuucaauu cacggacuaa    60
ggccaucaug aagauugcua uuguuugggc aauuucuuua gguaauuaac uuucuuggcc    120
aguagaauug cagcggcuau gcucaauacu uucggauuau guacugugaa caacguacag    180
acgucgacug guaa                                                      194

<210> SEQ ID NO 23
<211> LENGTH: 190
<212> TYPE: RNA
<213> ORGANISM: Mus musculus

<400> SEQUENCE: 23
ggaccgguau guagcaauac guaauccuau ugagcauagc cgguucaauu cgcggacuaa    60
ggccaucaug aagauugcca ucguuugggc aauaucaaua gguaauuaua ccuggccaua    120
gaauugcagc ggcuaugcuc aauaccuucg gauuauguac ugugaacaac cuacagacgu    180
cgacugguaa                                                           190

<210> SEQ ID NO 24
<211> LENGTH: 190
<212> TYPE: RNA
<213> ORGANISM: Rattus rattus

<400> SEQUENCE: 24
ggaccgguau guagcaauac guaauccuau ugagcauagc cgguucaauu cgcggacuaa    60
ggccaucaug aagauugcca ucguuugggc aauaucaaua gguaaauaua ccuggccaua    120
gaauugcagc ggcuaugcuc aauaccuucg gauuauguac ugugaacaac cuacagacgu    180
cgacugguaa                                                           190

<210> SEQ ID NO 25
<211> LENGTH: 147
<212> TYPE: RNA
<213> ORGANISM: Artificial Sequence
<220> FEATURE:
<223> OTHER INFORMATION: Section of the Homo sapien pre-mRNA 5-HT2C
      receptor sequence

<400> SEQUENCE: 25
```

```
uacguaaucc uauugagcau agccguuuca auucgcggac uaaggccauc auagagauug    60
cuauuguuug ggcaauuucu auagguaaau aaaacuuuuu ggccauaaga auugcagcgg   120
cuaugcucaa uacuuucgga uuaugua                                      147

<210> SEQ ID NO 26
<211> LENGTH: 195
<212> TYPE: RNA
<213> ORGANISM: Artificial Sequence
<220> FEATURE:
<223> OTHER INFORMATION: Section of the Homo sapien pre-mRNA 5-HT2C
      receptor sequence

<400> SEQUENCE: 26
ggaucgguau guagcaauac guaauccuau ugagcauagc cguuucaauu cgcggacuaa    60
ggccaucaug aagauugcua uuguuugggc aauuucuaua gguaaauaaa acuuuuuggc   120
cauaagaauu gcagcggcua ugcucaauac uuucggauua uguacuguga acaacguaca   180
gacgucgacu gguaa                                                   195

<210> SEQ ID NO 27
<211> LENGTH: 45
<212> TYPE: DNA
<213> ORGANISM: Artificial Sequence
<220> FEATURE:
<223> OTHER INFORMATION: Sequence product for the Vb splice site
      following control treatment

<400> SEQUENCE: 27
gaccggtatg tagcagtgcg taatcctgtt gagcatagcc ggttc                   45

<210> SEQ ID NO 28
<211> LENGTH: 45
<212> TYPE: DNA
<213> ORGANISM: Artificial Sequence
<220> FEATURE:
<223> OTHER INFORMATION: Sequence product for the Vb splice junction
      following treatment with oligo 5

<400> SEQUENCE: 28
gaccggtatg tagcagtgcg taatcctgtt gagcatagcc ggttc                   45
```

ANTISENSE OLIGONUCLEOTIDE MODULATORS OF SEROTONIN RECEPTOR 2C AND USES THEREOF

CROSS REFERENCE TO RELATED APPLICATIONS

This application is a national phase entry of international application serial number PCT/US2012/064319, filed Nov. 9, 2012, which claims priority benefit under 35 U.S.C §119 from U.S. patent application Ser. No. 61/707,592 filed Sep. 28, 2012 and U.S. patent application Ser. No. 61/558,407 filed Nov. 10, 2011, all of which are incorporated herein by reference.

BACKGROUND

Obesity is a serious health crisis with significant associated morbidity and mortality. It is estimated that about 64% of Americans are overweight or obese (roughly about 97 million adults) with a general belief that the proportion of overweight or obese people continues to rise. The prevalence of obesity worldwide is also believed to be increasing; the World Health Organization projects 700 million adults will be clinically obese (BMI≥30, body mass index; kg/m$^2$) by 2015. Co-morbidities include type 2 diabetes, hypertension, dyslipidemia, heart disease, stroke, arthritis, gallstones, liver problems, sleep apnea and even some cancers (e.g., endometrial, breast, prostate, and colon cancers). Higher body weights are also associated with increases in all-cause mortality.

Numerous treatments for obesity have been developed over time, although no treatment has ever gained general acceptance. One of these treatments, fenfluramine-phentermine (commonly known as "fen-phen"), which targets human serotonin receptor 2C (HTR2C or the 5-HT$_{2C}$ receptor) protein, was very effective in achieving weight loss, however, it was withdrawn due to side effects such as pulmonary hypertension and heart valve damage. Eventually, it was determined that the side effects of fen-phen were due to their agonist activity at several serotonin receptors.

The 5-HT$_{2C}$ receptor belongs to the family of seven transmembrane domain receptors (7TMRs) that signal to the internal cellular environment via heterotrimeric guanine nucleotide-binding proteins (G proteins) in response to stimulation by hormones, neurotransmitters and pharmacological ligands. The 5-HT$_{2C}$ receptor is found primarily in the central nervous system, and particularly in the epithelial cells of the choroid plexus. The receptor is implicated in a range of other diseases, ranging from obesity-linked conditions such as Prader-Willi Syndrome (PWS) and hyperphagia to psychological disorders to sleep disorders to addiction.

Existing pharmaceutical HTR2C agonists, such as fen-phen and locaserin, function through directly targeting the HTR2C protein. Such HTR2C agonists would not be effective in treating diseases like Prader-Willi Syndrome (PWS), in which the HTR2C protein is dramatically reduced or even absent.

SUMMARY

The present invention provides, among other things, oligonucleotide modulators of human 5'-HT2C receptor (HTR2C) and improved methods and compositions for treating HTR2C-related diseases, disorders or conditions based on such modulators.

As described in the Examples section, the present invention is, in part, based on the discovery that short antisense oligonucleotides that specifically target the Exon V/Intron V junction of the human HTR2C pre-mRNA can effectively drive the expression of the HTR2C Vb isoform by promoting Exon Vb inclusion, which in turn leads to the increased level of the strongest serotonin receptor, the non-edited receptor. As a result, such short antisense oligonucleotides can enhance the serotonin receptor activity in various cells and tissues including neurons, effecting various anti-obesity affects. As shown in the Examples, a short 18 mer antisense RNA oligonucleotide is surprisingly effective both in vitro and in vivo. It induces the expression of the HTR2C Vb isoform in the cell culture at a nanomolar concentration. Once injected to the brain, it can be successfully delivered to the neurons of hypothalamus and can effectively inhibit or reduce food intake in animals. Thus, antisense oligonucleotides provided by the present invention can be used to treat hyperphagia, obesity, and/or Prader Willi Syndrome.

In one aspect, the present invention provides an antisense oligonucleotide of 10-50 nucleotides in length comprising a sequence that permits specific hybridization to a target region of a human 5'-HT2C receptor (HTR2C) pre-mRNA under stringent conditions, wherein the target region includes a nucleotide sequence 5' UUGGCCAUAAGAAUUGCAGCGGCUAUGCUCAAUACU 3' (SEQ ID NO:1). In some embodiments, the stringent conditions include 50% formamide with 1 mg heparin at 42° C. with hybridization carried out overnight and a wash in 0.2×SSC at 65° C. for 15 minutes. In some embodiments, the sequence permits specific hybridization to nucleotides 1-18 of SEQ ID NO:1. In some embodiments, the sequence permits specific hybridization to nucleotides 10-27 of SEQ ID NO:1. In some embodiments, the sequence permits specific hybridization to nucleotides 19-36 of SEQ ID NO:1. In some embodiments, the sequence permits specific hybridization to nucleotides 19-30 of SEQ ID NO:1.

In various embodiments, the present invention provides an antisense oligonucleotide of 10-50 nucleotides in length comprising a sequence at least 70% identical to 10 or more contiguous nucleotides that appear in 5' AGUAUUGAGCAUAGCCGCUGCAAUUCUUAUGGCCAA 3' (SEQ ID NO:15). In some embodiments, the sequence is at least 70% identical to any of 5' UGCAAUUCUUAUGGCCAA 3' (SEQ ID NO:8), 5' CAUAGCCGCUGCAAUUCU 3' (SEQ ID NO:4), 5' AGUAUUGAGCAUAGCCGC 3' (SEQ ID NO:5), or 5' GAGCAUAGCCGC 3' (SEQ ID NO:7). In some embodiments, the sequence is selected from the group consisting of 5' UGCAAUUCUUAUGGCCAA 3' (SEQ ID NO:8), 5' CAUAGCCGCUGCAAUUCU 3' (SEQ ID NO4), 5' AGUAUUGAGCAUAGCCGC 3' (SEQ ID NO:5), or 5' GAGCAUAGCCGC 3' (SEQ ID NO:7), and combination thereof. In some embodiments, the sequence is 5' AGUAUUGAGCAUAGCCGC 3' (SEQ ID NO:5). In some embodiments, the sequence is 5' GAGCAUAGCCGC 3' (SEQ ID NO:7).

In various embodiments, at least one of the nucleotides in the oligonucleotide is a chemically modified oligonucleotide. For example, in some embodiments, the chemically modified oligonucleotide is 2'O methyl modified. In some embodiments, the chemically modified oligonucleotide is thiophosphate modified. In some embodiments, the chemically modified oligonucleotide is modified to be a locked nucleic acid.

In another aspect, the present invention provides a pharmaceutical composition including an antisense oligonucleotide of any of the embodiments described herein and a pharmaceutically acceptable carrier.

In a further aspect, the present invention provides a method of modulating human 5'-HT2C receptor (HTR2C) activity in a cell including delivering an antisense oligonucleotide of any of the embodiments described herein. In some embodiments, the cell is a neuron. In some embodiments, the neuron is in the hypothalamus region of the brain. In some embodiments, an antisense oligonucleotide 5' AGUAUUGAGCAUAGCCGC 3' (SEQ ID NO:5) is administered. In some embodiments, the antisense oligonucleotide is administered at a concentration of or greater than about 5 nM (e.g., of or greater than about 10 nM, 15 nM, 20 nM, 25 nM, 30 nM, 35 nM, 40 nM, 45 nM, or 50 nM).

In various embodiments, the antisense oligonucleotide is administered at an amount effective to increase the level of the HTR2C Vb isoform as compared to a control level. In some embodiments, the antisense oligonucleotide is administered at an amount effective to increase the level of the HTR2C Vb isoform by at least about 20%, 40%, 60%, 80%, 1, 2, 3, 4, 5, 6, 7, 8, 9, 10, 11, 12, 13, 14, 15, 16, 17, 18, 19 or 20 fold as compared to a control level. In some embodiments, a suitable control level is the level of the HTR2C Vb isoform in otherwise identical cells but without treatment (e.g., the HTR2C Vb isoform level before the treatment). In some embodiments, a suitable control level is a level indicative of the HTR2C Vb isoform expression in a patient suffering from hyperphagia, obesity, PWS or other HTR2C-related diseases, disorders or condition.

Among other things, the present invention provides various methods for treating diseases, disorders or conditions associated with HTR2C dysfunction. In some embodiments, the present invention provides a method of reducing food consumption including administering to a subject in need of treatment an antisense oligonucleotide described herein. In certain embodiments, the administration of an antisense oligonucleotide of the invention results in reduction of food consumption by at least about 10%, 20%, 30%, 40%, 50%, 60%, 70%, 80%, 90%, 95%, or more as compared to a pre-treatment or no-treatment control.

In some embodiments, the present invention provides a method of treating hyperphagia including administering to a subject in need of treatment an antisense oligonucleotide described herein.

In some embodiments, the present invention provides a method of treating obesity including administering to a subject in need of treatment an antisense oligonucleotide described herein.

In some embodiments, the present invention provides a method of treating Prader-Willi syndrome including administering to a subject in need of treatment an antisense oligonucleotide described herein.

It will be appreciated the oligonucleotide may be delivered to the subject by any appropriate method. In some embodiments, the antisense oligonucleotide is administered directly to the brain of the subject.

In various embodiments, the present invention provides a kit including an antisense oligonucleotide of any one of the embodiments described herein and tools for administration to the brain of a mammal.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DEFINITIONS

Figure 1:
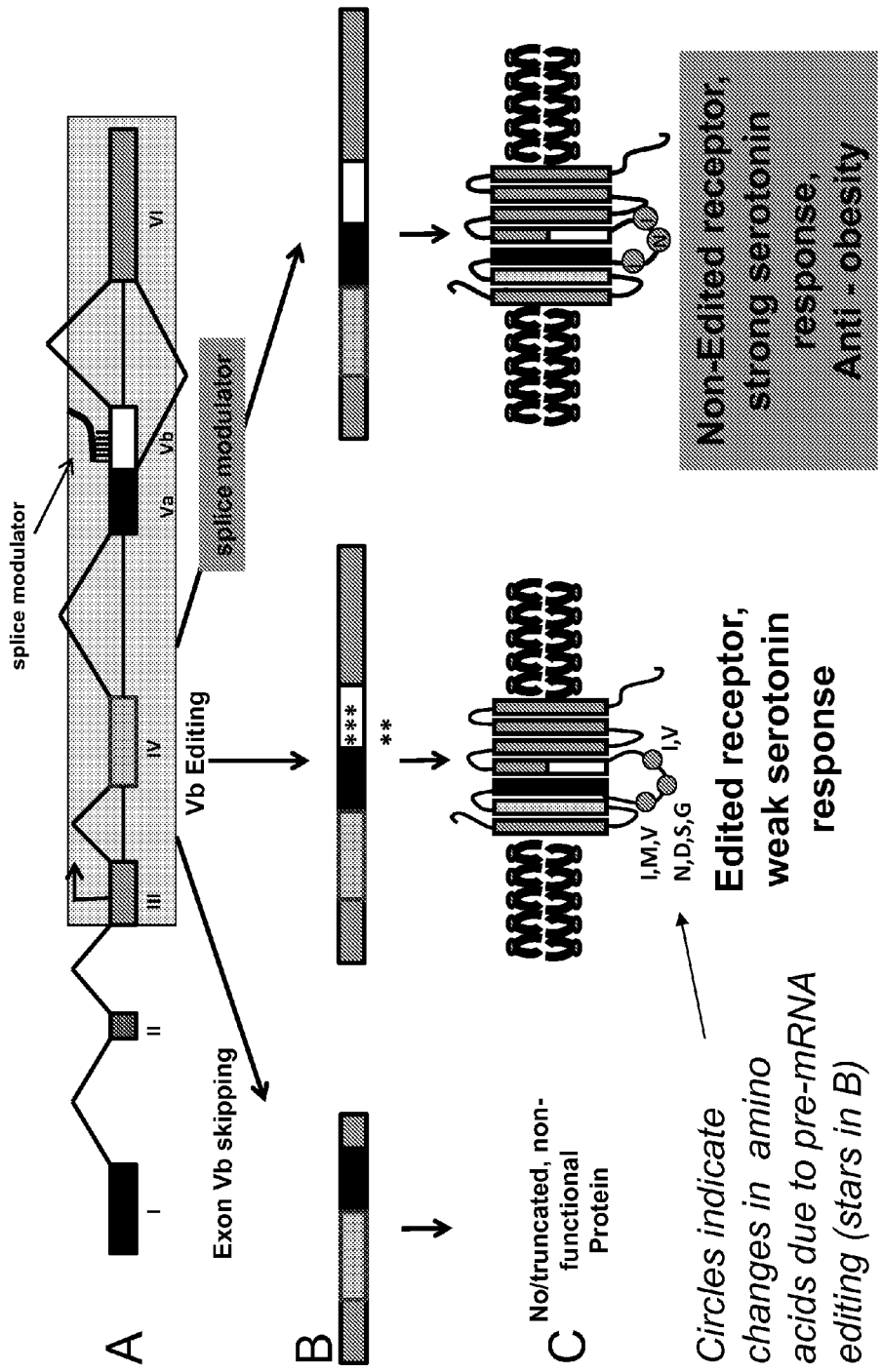
FIG. 1 illustrates regulation pathways of the serotonin 2C receptor.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition.

Biologically active: As used herein, the phrase "biologically active" refers to a characteristic of any agent that has activity in a biological system, in vitro or in vivo (e.g., in an organism). For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Membrane penetrating peptide: As used herein, the term "membrane-penetrating peptide" refers to any peptide that is capable of facilitating cellular uptake of a molecule cargo (e.g., from nanosize particles to small molecules, proteins, nucleic acids). A membrane-penetrating peptide can be associated with a molecular cargo through chemical linkage, covalent bonds or non-covalent interactions. Exemplary membrane-penetrating peptides include, but are not limited to, HIV-TAT, Antp, penetratin, polylysine, polyarginie, VP22, Syn B1, PTD-4, Pep-1, transportan and FGF-4 peptides. Suitable membrane-penetrating peptides can be produced using recombinant and synthetic methods or purified from natural sources and encompass both naturally-occurring sequences and modified sequences that retain membrane penetrating ability. In many embodiments, membrane-penetrating peptides are also capable of penetrating more then one type of cell membrane. In some embodiments, the terms "membrane-penetrating peptides" and "cell penetrating peptides" are used interchangeably.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measured by formation of high molecular weight (HMW) aggregates, loss of enzyme activity, generation of peptide fragments and shift of charge profiles. For nucleotide stability, it can be measured by formation of base decomposition products, loss of binding to a target and generation of fragments.

Stringent conditions: As used herein, the term "stringent conditions" refers to a set of conditions for nucleic acid hybridization that allows an oligonucleotide specifically binds to a sequence that is complementary to the oligonucleotide. Typical exemplary stringent conditions include 50% formamide with 1 mg heparin at 42° C. with hybridization carried out overnight and a wash in 0.2×SSC at 65° C. for 15 minutes.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% A or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

CNS delivery: As used herein, the phrase "CNS delivery" or "injection to the brain" typically refers to an administration method that bypasses the blood brain barrier and delivers therapeutic agents directly to the CNS or brain area.

Target tissues: As used herein, the term "target tissues" refers to any tissue that is affected by the defects in or lower than desired activity from the 5-$HT_{2C}$ receptor, especially the central nervous system. In some embodiments, target tissues include those tissues in which there is an abnormality in the editing of the RNA for the 5-$HT_{2C}$ receptor. In some embodiments, target tissues include those tissues that display disease-associated pathology, symptom, or feature. As used herein, a target tissue may be a brain target tissue, a spinal cord target tissue an/or a peripheral target tissue. Exemplary target tissues are described in detail below.

Therapeutically effective amount: As used herein, the term "therapeutically effective amount" refers to an amount of a therapeutic agent which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific agent employed; the duration of the treatment; and like factors as is well known in the medical arts.

Treatment: As used herein, the term "treatment" (also "treat" or "treating") refers to any administration of a therapeutic agent (e.g., oligonucleotide) that partially or completely alleviates, ameliorates, relieves, inhibits, delays onset of, reduces severity of and/or reduces incidence of one or more symptoms or features of a particular disease, disorder, and/or condition (e.g., hyperphagia, obesity, Prader Willi Syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides, among other things, improved compositions and methods for modulating human 5'-HT2C receptor (HTR2C) activity and for treatment of a disease, disorder or condition associated with HTR2C. In particular, the present invention is based on antisense oligonucleotide modulators of HTR2C that enhance the HTR2C activity by promoting Exon Vb inclusion, resulting in increased expression of the HTR2C Vb isoform, which in turn leads to the increased level of the strong serotonin receptor, the non-edited receptor. In some embodiments, the present invention provides antisense oligonucleotides that specifically target the Exon V/Intron V junction of a human 5'-HT2C receptor (HTR2C) pre-mRNA. In this application, the terms "exon 5", "exon V", "Exon 5" and "Exon V" are used inter-changeably, and the terms "intron 5", "intron V", "Intron 5" and "Intron V" are also used inter-changeably.

Various aspects of the invention are described in detail in the following sections. The use of sections is not meant to limit the invention. Each section can apply to any aspect of the invention. In this application, the use of "or" means "and/or" unless stated otherwise.

Human Serotonin Receptor 2C(HTR2C) and Related Diseases and Conditions

The HTR2C belongs to the family of seven transmembrane domain receptors (7TMRs) that signal to the internal cellular environment via heterotrimeric guanine nucleotide-binding proteins (G proteins) in response to stimulation by hormones, neurotransmitters and pharmacological ligands. The HTR2C significantly regulates mood, anxiety, feeding, and reproductive behavior. The HTR2C is found primarily in the central nervous system, and particularly in the epithelial cells of the choroid plexus. The receptor is implicated in a range of other diseases, ranging from obesity-linked conditions such as Prader-Willi Syndrome (PWS) and hyperphagia to psychological disorders to sleep disorders to addiction. In particular, it was reported that the 5-HT$_{2C}$ receptor may underlie the insatiable appetite in Prader-Willi syndrome.

The activity of the HTR2C is partly regulated by RNA editing. It has been reported that there existed different isoforms of HTR2C with altered G protein-coupling efficacy generated by RNA editing, which converts genomically encoded adenosine residues into inosines. See, Wang Q., et al. "Altered G Protein-Coupling Functions of RNA Editing Isoform and Splicing Variant Serotonin$_{2C}$ Receptors," *J. Neurochem.*, 74, 1290-1300 (2000), the teachings of which are hereby incorporated by reference.

In particular, two alternative splicing donor sites exist in Exon V, which gives rise to Exon Va and Exon Vb. Exon Vb skipping generates the HTR2C Va splice isoform, which results in a truncated and non-functional protein. Exon Vb inclusion results in the HTR2C Vb splice isoform, which may give rise to edited receptor and non-edited receptor as a result of RNA editing mechanism. The edited version demonstrates weak serotonin response while the non-edited version has strong serotonin response. Expression of the non-edited receptor prevents the obesity and hyperphagia associated with the loss of the HTR2C in transgenic mouse model, suggesting that the non-edited receptor is the major anti-obesity form of the HTR2C. A diagram illustrating regulation of the serotonin receptor through alternative splicing and RNA editing is shown in FIG. 1.

An alternative splicing region covering the human HTR2C Exon5/Intron5 boundary is shown below (uppercase: Exon5, lowercase: Intron5).

(SEQ ID NO: 2)
ATTATGTCTGGCCACTACCTAGATATTTGTGCCCCGTCTGGATTTCTTTA

GATGTTTTATTTTCAACAGCGTCCATCATGCACCTCTGCGCTATATCGCT

-continued

GGATCG*GTATGTAGCAATACGTAATCCTATTGAGCATAGCCGTTTCAAT

TCGCGGACTAAGGCCATCATGAAGATTGCTATTGTTTGGGCAATTTCTAT

AG*gtaaataaacttttt<u>ggccataagaattgcagcggctatgctcaat</u>

<u>actttcggattatgtactgtgaacaacgtacagacgtcgactggtaa</u>
*indicate 5A and 5B splice donor sites.

Modulators of HTR2C

As discussed in the Examples below, the present inventors have successfully identified antisense oligonucleotide modulators that change the splicing of the HTR2C. In particular, those modulators enhance or promote Exon Vb inclusion resulting in increased non-edited version of the HTR2C.

Antisense Oligonucleotides

Among other things, the present invention provides antisense oligonucleotides useful for modulation of HTR2C. An antisense oligonucleotide suitable for the present invention includes any oligonucleotide that is capable of modulating HTR2C or that can rescue or ameliorate one or more diseases, disorders or conditions associated with HTR2C.

In some embodiments, provided antisense oligonucleotides are capable of hybridizing or binding to a target region of HTR2C pre-mRNA such that it changes splicing of the HTR2C. In some embodiments, provided antisense oligonucleotides are capable of hybridizing or binding to a target region of HTR2C pre-mRNA such that it enhances or promotes Exon Vb inclusion resulting in the HTR2C splice isoform Vb.

It will be appreciated that hybridization of an antisense oligonucleotide to a target region of HTR2C pre-mRNA may be performed in vitro or in vivo. Hybridization may be performed under low, medium, and/or stringent hybridization conditions, as is well known in the art. In general, stringent hybridization conditions refer to standard hybridization conditions under which nucleic acid molecules, including oligonucleotides, are used to identify molecules having complementary nucleic acid sequences. Stringent hybridization conditions typically permit binding between nucleic acid molecules having at least about 50%, 55%, 60%, 65%, 70%, 75%, 80%, 85%, 90%, 95%, or more nucleic acid sequence identity. Standard conditions are disclosed, for example, in Sambrook et al., 1989, Molecular Cloning: A Laboratory Manual, Cold Spring Harbor Labs Press, the contents of which is incorporated herein by reference in its entirety. Formulae to calculate the appropriate hybridization and wash conditions to achieve hybridization permitting 50%, 40%, 30%, 20%, 10%, 5% or less mismatch of nucleotides are available in the art, for example, in Meinkoth et al., 1984, Anal. Biochem. 138, 267-284; the contents of which is incorporated herein by reference in its entirety. It will be appreciated that hybrids between oligonucleotides (14-20 bp) and immobilized DNA show decreased stability and should be taken into account when defining optimal conditions for their hybridization.

Hybridization condition stringency can be affected by buffer ionic strength, base composition of the nucleotide, the length of the shortest chain in the duplex (n), and the concentration of helix destabilizing agents such as formamide. For example, hybridization stringency can be altered by adjusting the salt and/or formamide concentrations and/or by changing the temperature. The stringency can be adjusted either during the hybridization step, or in post hybridization washes. An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of stringent wash conditions is a 0.2×SSC wash at 65° C. for 15 minutes. In some embodiments, a high stringency wash is preceded by a low stringency wash to remove back-ground probe signal. An example medium stringency wash for a duplex of, e.g., more than 100 nucleotides, is 100×SSC at 45° C. for 15 minutes. An example low stringency wash for a duplex of, e.g., more than 100 nucleotides, is 4×SSC at 40° C. for 15 minutes. In general, a signal to noise ratio of 2× (or higher) than that observed for an unrelated probe in the particular hybridization assay indicates detection of a specific hybridization.

In some embodiments, provided oligonucleotides bind to a target region of HTR2C including a nucleotide sequence found at the exon5-intron5 boundary. Sequences of the human and mouse HTR2C exon5/intron5 sequence are shown in Table 1 (uppercase: exon5, lowercase: intron5).

In some embodiments, provided oligonucleotides bind to a target region that is substantially homologous to SEQ ID NO:2. In some embodiments, a suitable HTR2C target region includes a nucleotide sequence that has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2.

In some embodiments, provided oligonucleotides bind to a target region that is substantially identical to SEQ ID NO:2. For example, provided oligonucleotides bind to a target region that has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2.

In some embodiments, provided oligonucleotides bind to a target region that is substantially homologous to SEQ ID NO:3. For example, provided oligonucleotides bind to a target region that has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3.

TABLE 1

HTR2C Exon5/Intron5 sequence

| | | |
|---|---|---|
| human HTR2c exon5/intron5 | ATTATGTCTGGCCACTACCTAGATATTTGTGCCCCGTCTGGATTTCTTTAGATGTTT TATTTTCAACAGCGTCCATCATGCACCTCTGCGCTATATCGCTGGATCGGTATGTAG CAATACGTAATCCTATTGAGCATAGCCGTTTCAATTCGCGGACTAAGGCCATCATGA AGATTGCTATTGTTTGGGCAATTTCTATAGgtaaataaaActttttggccataagaa Ttgcagcggctatgctcaatactttcggattatgtactgtgaacaacgtacagacgt cgactggtaa | SEQ ID NO: 2 |
| mouse HTR2c exon5/intron5 | ATTATGTCTGGCCTTTACCTAGATATTTGTGCCCCGTCTGGATTTCACTAGATGTGC TATTTTCAACTGCGTCCATCATGCACCTCTGCGCCATATCGCTGGACCGGTATGTAG CAATACGTAATCCTATTGAGCATAGCCGGTTCAATTCGCGGACTAAGGCCATCATGA AGATTGCCATCGTTTGGGCAATATCAATAGgtaattatacctggccatagaatTgca Gcggctatgctcaatacctttcggattatgtactgtgaacaacctacagacgtcgact ggtaa | SEQ ID NO: 3 |

In some embodiments, provided oligonucleotides bind to the exon5-intron5 boundary regions shown above (SEQ ID NO:2 or SEQ ID NO:3). In some embodiments, provided oligonucleotides bind to the intron regions shown in Table 1. In some embodiments, provided oligonucleotides bind to a target region including a nucleotide sequence 5' UUGGC-CAUAAGAAUUGCAGCGGCUAUGCUCAAUACU 3' (SEQ ID NO:1). In some embodiments, provided oligonucleotides bind to nucleotides 1-18 of SEQ ID NO:1. In some embodiments, provided oligonucleotides bind to nucleotides 10-27 of SEQ ID NO:1. In some embodiments, provided oligonucleotides bind to nucleotides 19-36 of SEQ ID NO:1. In some embodiments, provided oligonucleotides bind to nucleotides 19-30 of SEQ ID NO:1.

Provided oligonucleotides may bind to a target region of a serotonin receptor 2C from a different species. Thus, in some embodiments, provided oligonucleotides bind to a target region that is substantially homologous to SEQ ID NO:1. For example, provided oligonucleotides may bind to a target region that has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1.

In some embodiments, provided oligonucleotides bind to a target region that is substantially identical to SEQ ID NO:1. For example, provided oligonucleotides bind to a target region that has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

In some embodiments, provided oligonucleotides bind to a target region that is substantially identical to SEQ ID NO:3. For example, provided oligonucleotides bind to a target region that has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3.

In various embodiments, the present invention provides an antisense oligonucleotide of 10-50 nucleotides in length comprising a sequence at least 70% (e.g., 75%, 80%, 85%, 90%, 91%, 92%, 93%, 94%, 95%, 96%, 97%, 98%, 99% or more) identical to 10 or more contiguous nucleotides that appear in 5' AGUAUUGAGCAUAGCCGCUGCAAUUC-UUAUGGCCAA 3' (SEQ ID NO:9), which is a complementary sequence of a target region defined by SEQ ID NO:1.

Exemplary short antisense oligonucleotides suitable for the present invention are listed in Table 2:

TABLE 2

Short Antisense RNA Oligonucleotides

| Oligo # | Sequence (5'-3') | SEQ ID NO: |
|---|---|---|
| 2 | CAUAGCCGCUGCAAUUCU | 4 |
| 5 | AGUAUUGAGCAUAGCCGC | 5 |
| 5-5 | AGUAUUGAGCAU | 6 |
| 5-3 | GAGCAUAGCCGC | 7 |
| 5-10 | GCAUAGCCGC | 16 |
| 6 | UGCAAUUCUUAUGGCCAA | 8 |

In some embodiments, an antisense oligonucleotide in accordance with the present invention has a sequence that is at least 50%, 55%, 60%, 65%, 70%, 75%, 80%, 85%, 90%, 95%, 98%, or 99% identical to any of SEQ ID NO: 4, SEQ ID NO:5, SEQ ID NO:6, SEQ ID NO:7, SEQ ID NO: 8, and SEQ ID NO:16. In some embodiments, the sequence is selected from SEQ ID NO: 4, SEQ ID NO:5, SEQ ID NO:6, SEQ ID NO:7, SEQ ID NO: 8, SEQ ID NO:16, and combinations thereof. In some embodiments, the sequence is SEQ ID NO:7. In some embodiments, the sequence is SEQ ID NO:5.

It will be appreciated that an antisense oligonucleotide in accordance with the present invention may be of any appropriate length. For example, in some embodiments, an antisense oligonucleotide is 10-50 nucleotides in length. In some embodiments, an antisense oligonucleotide is 10-30 nucleotides in length. In certain embodiments, an antisense oligonucleotide is 15-40 nucleotides in length. In some embodiments, an antisense oligonucleotide is 10, 11, 12, 13, 14, 15, 16, 17, 18, 19, 20, 22, 24, 26, 28, 30, 32, 34, 36, 38, 40, 42, 44, 46, 48, or 50 nucleotides in length "Percent (%) nucleic acid sequence identity" with respect to the nucleotide sequences identified herein is defined as the percentage of nucleotides in a candidate sequence that are identical with the nucleotides in the reference sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology*, 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

Chemical Modifications

RNA molecules, including the antisense oligonucleotides described herein, may be chemically modified to change (e.g., increase or decrease) intracellular stability and half-life. Possible modifications include the addition of flanking sequences at the 5' and/or 3' ends of the molecule or the use of phosphorothioate (also known as thiophosphate) linkages rather than phosphodiesterase linkages within the backbone of the molecule. In addition, one or more ribose groups may be modified to add a methyl moiety to the 2'-OH to form a 2'-methoxy moiety (referred to as 2'O-methyl-modified). Also, the 2'-OH moiety can be linked to the or 3' or 4'-carbon of ribose by a methylene or ethylene linker, typically a methylene linker to the 4'-carbon, to form a "locked nucleic acid" (see WO 98/39352 and WO 99/14226, the contents of which are incorporated herein by reference).

In certain embodiments, chemical modification also includes the use of nontraditional bases such as inosine, queosine, and wybutosine, as well as acetyl-, methyl-, thio-, and other similarly modified forms of adenine, cytidine, guanine, thymine, and uridine, which are not as easily recognized by endogenous endonucleases. Examples of modified bases include uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; and O- and N-alkylated nucleotides, e.g., N6-methyl adenosine.

In certain embodiments, the sugar moiety can be modified, typically at the 2'-OH of ribose. Examples of such modifications include instances where the 2' OH-group is replaced by a group selected from H, OR, R, halo, SH, SR, $NH_2$, NHR, $NR_2$ or ON, where R is $C_1$-$C_6$ alkyl, alkenyl or alkynyl and halo is F, Cl, Br or I.

Further, chemical modification can encompass modified backbones such as morpholino and/or further non-natural internucleoside linkages such as siloxane, sulfide, sulfoxide, sulfone, sulfonate, sulfonamide, and sulfamate; formacetyl and thioformacetyl; alkene-containing; methyleneimino and methylenehydrazino; amide, and the like.

One or more nucleotides (or linkages) within the sequences described herein can be modified. For example, a 20-mer oligonucleotide may contain 1, 2, 3, 4, 5, 6, 7, 8, 9, 10, 11, 12, 13, 14, 15, 16, 17, 18, 19 or 20 modified nucleotides. In certain embodiments, a modified oligonucleotide will contain as few modified nucleotides as are necessary to achieve a desired level of in vivo stability and/or bioaccessibility while maintaining cost effectiveness.

Therapeutic Uses

Antisense oligonucleotide modulators of HTR2C described herein may be used to treat various HTR2C related diseases, disorders and conditions.

Treatment of Prader-Willi Syndrome

Prader-Willi Syndrome (PWS) is a genetic disorder, with a gene missing on chromosome 15, which is characterized by hyperphagia. People with this condition are typically obese, have reduced muscle tone and mental ability, and have sex glands that produce little or no hormones.

Newborns with PWS typically have several of the following symptoms: are small for gestational age; have genitals that are not well developed (in boys, the testicles cannot be felt in the scrotum); have problems sucking and swallowing, and often do not gain weight; have poor muscle tone (hypotonia); often have a weak cry; delayed motor development; and show changes in the face, such as "almond-shaped" eyes and a small, downturned mouth.

Affected children, beginning at about age 1 to 4, generally develop an intense craving for food, leading to weight gain and morbid obesity. These children also tend to have shorter stature and below-normal IQ. In later childhood and in adulthood, the symptoms of PWS may include: incomplete sexual development (hypogonadism, infertility); low muscle mass; short stature; scoliosis; sleep disorders (disruptions of the normal sleep cycle, sleep apnea); compulsive-like behaviors; abnormal glucose tolerance; above normal level of the hormone insulin in the blood; failure to respond to luteinizing hormone releasing factor; high carbon dioxide levels; lack of oxygen supply; right-sided heart failure; and knee and hip problems.

Antisense oligonucleotide modulators of HTR2C described herein may be used to treat the PWS syndrome. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or completely alleviation, amelioration, relief, inhibition, delaying onset, reducing severity and/or incidence of one or more symptoms in an PWS patient, including, but not limited to, hyperphagia, below-normal IQ, low muscle mass; short stature; scoliosis; sleep disorders (disruptions of the normal sleep cycle, sleep apnea); compulsive-like behaviors; abnormal glucose tolerance; above normal level of the hormone insulin in the blood; failure to respond to luteinizing hormone releasing factor; high carbon dioxide levels; lack of oxygen supply; right-sided heart failure; and knee and hip problems.

In some embodiments, treatment refers to reduced food intake or consumption in a subject in need of treatment. In certain embodiments, the amount of food intake or consumption may be reduced by at least about 10%, 20%, 30%, 40%, 50%, 60%, 70%, 80%, 90%, 95%, or more as compared to a pre-treatment or no-treatment control (e.g., the amount of food intake or consumption by the same subject pre-treatment or the amount of food intake or consumption by a control subject with similar diseased or developmental stage but without treatment).

In some embodiments, treatment refers to improved body weight loss (e.g., total weight loss, percent body weight loss per week, per month, per two months, per six months, etc.). In certain embodiments, total body weight loss is, on average, about 0.1 kg, about 0.2 kg, about 0.3 kg, about 0.4 kg, about 0.5 kg, about 0.6 kg, about 0.7 kg, about 0.8 kg, about 0.9 kg, about 1 kg, about 1.1 kg, about 1.2 kg, about 1.3 kg, about 1.4 kg, about 1.5 kg, about 1.6 kg, about 1.7 kg, about 1.8 kg, about 1.9 kg, about 2 kg, about 2.1 kg, about 2.2 kg, about 2.3 kg, about 2.4 kg, about 2.5 kg, about 2.6 kg, about 2.7 kg, about 2.8 kg, about 2.9 kg, about 3 kg, or more, per week. In some embodiments, percent body weight loss is a decrease by, on average, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more per week. As used herein, percent body weight loss is determined by comparing the total body weight loss to the base total body weight before the loss.

In some embodiments, treatment refers to reduced or prevented weight gain (e.g., total weight gain, percent body weight gain per week, per month, per two months, per six months, etc.). In some embodiments, total body weight gain is, on average, less than about 0.1 kg, about 0.2 kg, about 0.3 kg, about 0.4 kg, about 0.5 kg, about 0.6 kg, about 0.7 kg, about 0.8 kg, about 0.9 kg, about 1 kg, about 1.1 kg, about 1.2 kg, about 1.3 kg, about 1.4 kg, about 1.5 kg, about 1.6 kg, about 1.7 kg, about 1.8 kg, about 1.9 kg, about 2 kg, about 2.1 kg, about 2.2 kg, about 2.3 kg, about 2.4 kg, about 2.5 kg, about 2.6 kg, about 2.7 kg, about 2.8 kg, about 2.9 kg, or about 3 kg, per week. In some embodiments, percent body gain is, on average, less than about 0.1%, about 0.5%, about 1%, about 1.5%, about 2%, about 2.5%, about 3%, about 3.5%, about 4%, about 5%, about 10%, about 15%, about 20%, or about 25%, per week. As used herein, percent body weight gain is determined by comparing the total body weight gain to the base total body weight before the gain.

In other embodiments, treatment refers to increased survival (e.g., survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with Prader-Willi Syndrome without treatment. In some embodiments, treatment according to the present invention results in an increased life expectancy of a patient by more than about 1 month, about 2 months, about 3 months, about 4 months, about 5 months, about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease form without treatment. In some embodiments, treatment according to the present invention results in long term survival of a patient. As used herein, the term "long term survival" refers to a survival time or an increased life expectancy of longer than about 10 years, 15 years, 20 years, 25 years, 30 years or longer.

Treatment of other HTR2C-Associated Diseases

Inventive methods and compositions of the present invention are particularly useful for treating those diseases having a 5'-HT2C receptor (HTR2C) etiology, component or relationship. Giuseppe's 5-HT2C *Receptors in the Pathophysiology of CNS Disease*, $1^{st}$ Edition, G. Di Giovanni et. al. (Humana Press, 2010; incorporated herein by reference) discloses various diseases associated, caused and/or affected by HTR2C dysregulation. Representative diseases having an HTR2C etiology or component include, for example and without limitation, metabolic disorders such as obesity, hyperphagia, lack of satiety, and diabetes; psychiatric disorders such as schizophrenia (Sodhi, M, S. et. al., *RNA editing of the 5-HT(2C) receptor is reduced in schizophrenia*, Molecular Psychiatry, 2001; (6): 373-9; incorporated herein by reference), depression (Iwamoto, K, et. al., *Estimating RNA editing efficiency of five editing sites in the serotonin 2C receptor by pyrosequencing*, RNA, 2005; (11): 1596-1603; incorporated herein by reference), suicidal tendencies (Niswender, C, M., et. al., *RNA editing of the human serotonin 5-HT2C receptor: alterations in suicide and implications for erotonergic pharmacotherapy*, Neuropsychopharmacology, 2001; (24): 478-91, incorporated herein by reference) and bipolar disorder; epilepsy including sensitivity to seizure and a reduced seizure threshold; addictive disorders (e.g., cocaine addiction, tetrahydrocannabinol addiction, nicotine addition); and sleep disorders (insomnia, abnormal REM sleep). Several of the listed methods involve delivery of one of the compositions described herein to neurons, such as those located in the brain.

Metabolic Disorders

A first group of conditions treated according to the present invention are metabolic disorders. Such metabolic disorders can be caused by insufficient metabolism of calorie intake (e.g., obesity), elevated blood glucose (e.g., diabetes) or an inability to control appetite (e.g., hyperphagia).

Obese individuals or individuals suffering from obesity are generally individuals having a body mass index (BMI) of at least 25 or greater or at least 30 or greater. Obesity may or may not be associated with insulin resistance. Obesity can lead to other conditions such as type 2 diabetes, hypertension, dyslipidemia, heart disease, stroke, arthritis, gallstones, liver problems, sleep apnea and some cancers (e.g., endometrial, breast, prostate, and colon cancers).

Diabetes refers to high blood sugar or ketoacidosis, as well as chronic, general metabolic abnormalities arising from a prolonged high blood sugar status or a decrease in glucose tolerance. Diabetes encompasses both the type I and type II (Non Insulin Dependent Diabetes Mellitus or NIDDM) forms of the disease. Subjects with type II diabetes often suffer from insulin resistance, which refers to a state in which a normal amount of insulin produces a subnormal biologic response relative to the biological response in a subject that does not have insulin resistance. An insulin resistance disorder generally refers to any disease or condition that is caused by or contributed to by insulin resistance.

Hyperphagia, also known as polyphagia, refers to excessive hunger and/or an excessive impulse to eat.

Psychiatric Disorders

Psychiatric disorders that can be treated using the compositions and methods described herein include, but are not limited to, psychosis, schizophrenia, anxiety (Hackler, E, A., et. al., 5-*HT*(2*C*) *receptor RNA editing in the amygdala of C57BL/6J, DBA/2J, and BALB/cJ mice*, Neurosci Res, 2006; (55): 96-104; incorporated herein by reference) (including generalized anxiety disorder, panic disorder, social phobia, obsessive compulsive disorder, and post-traumatic stress disorder (PTSD)), suicidal tendencies and mood disorders (including depression, mania, bipolar disorders). In certain embodiments, one or more of schizophrenia, depression, suicidal tendencies and bipolar disorder are treated.

Epilepsy

Epilepsy and associated conditions represent another group of disorders that can be treated using the compositions and methods described herein. Epilepsy is a common chronic neurological disorder that is characterized by recurrent unprovoked seizures. These seizures may be transient signs and/or symptoms due to abnormal, excessive or synchronous neuronal activity in the brain. Illustrative examples of epileptic seizures treatable with the methods and compositions described herein include tonic-clonic, clonic (with or without tonic features), absence (typical or atypical), myoclonic absence, tonic, myoclonic, massive bilateral myoclonus, negative myoclonus, eyelid myclonia (accompanied or not by absence seizures), myoclonic-atonic, atonic, reflex, focal sensory (with elementary sensory symptoms, such as occipital and parietal lobe seizures, or experiential sensory symptoms, such as temporo parieto occipital junction seizures, and the like), focal motor (with elementary clonic motor signs, with asymmetrical tonic motor signs or seizure, such as supplementary motor seizures, with typical automatisms, also referred to as temporal lobe automatisms, such as mesial temporal lobe seizures, with hyperkinetic automatisms, with focal negative myoclonus, and the like), inhibitory motor, gelastic, hemiclonic, secondarily generalized, reflex seizures in focal epilepsy syndromes, generalized tonic-clonic status epilepticus, clonic status epilepticus, absence status epilepticus, tonic status epilepticus, myoclonic status epilepticus, epilepsia partialis continua, aura continua, limbic status epilepticus, hemiconvulsive status epilepticus. Methods of the invention include reducing the likelihood of epilepsy and reducing the severity of a seizure.

Addictive Disorders

Another group of disorders that can be treated using the compositions and methods described herein are addictive disorders, particularly those disorders where serotonin plays a role in maintaining the addictive behavior. Typically, addiction is classified as a behavioral disorder, characterized by a compulsive search for the product that causes this dependency, despite the harmful consequences on the health, family, professional life, etc. of which the dependent person is fully aware. Examples of addictions treatable by the methods described herein include cocaine addiction, tetrahydrocannabinol addiction, opioid addiction and nicotine addition. Treatment can be assessed, for example, by reduction in cravings, reduction in use of a substance, reduction of relapse of addiction.

Sleep Disorders

The present invention also provides compositions and methods that treat sleep disorders. Sleep disorders include an inability to fall asleep or stay asleep, collectively known as insomnia. Insomnia can be transient or chronic. Sleep disorders also include conditions where the quality of sleep is disturbed, such as when a subject has abnormal REM sleep.

Autonomic Dysregulation

The present invention also provides compositions and methods that treat disease associated with dysregulation of one or more physiological functions controlled by the autonomic nervous system. Autonomic dysregulation (Dysautonomia) includes an inability to maintain homeostasis and regulate a response to basic changes such as temperature, walking, sitting, sleeping, eating, desiring, digesting food or thirst. Autonomic dysregulation also includes conditions related to thermal regulation, in which the subject resides is a state of hypo- and/or hyperthermia. Data suggests that modulation of HTR2C, such as with a HTR2C agonist, can play an important role in controlling thermal regulation (Deecher, Darlene, C., et. al., *Alleviation of Thermoregulatory Dysfunction with the New Serotonin and Norepinephrine Reuptake Inhibitor Desvenlafaxine Succinate in Ovariectomized Rodent Models*, Neuroendocrinology, 2007; (3): 1376; and Findlay, J. D., et. al, *The mechanism of body temperature changes induced by intraventicular injections of adrenaline, noradrenaline and 5-hydroxytryptamine in the ox (bos Taurus)*, The journal of Physiology, 1967; (189): 329-336; both of which are incorporated herein by reference.)

Pharmaceutical Compositions

The present invention further provides pharmaceutical compositions comprising therapeutic actives in accordance with the invention (e.g., antisense oligonucleotides), together with one or more pharmaceutically acceptable excipients. Such pharmaceutical compositions may optionally comprise one or more additional therapeutically-active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$. Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference).

In some embodiments, liposomes may be used to deliver antisense oligonucleotides described herein. As used herein, a liposome is an artificially-prepared vesicle composed of a lipid bilayer. Liposomes can be prepared by disrupting biological membranes (such as by sonication). Liposomes may include natural phospholipids, or mixed lipid chains with surfactant properties (e.g., egg phosphatidylethanolamine) A liposome design may employ surface ligands for targeting desired target tissues.

Administration

The present invention provides methods of administering an effective amount of a therapeutic active described herein (e.g., an antisense oligonucleotide) to a subject in need of treatment.

Antisense oligonucleotides described herein may be administered through various administration routes including, but not limited to, intravenous, subcutaneous, intramuscular, parenteral, transdermal, or transmucosal (e.g., oral or nasal). In some embodiments, antisense oligonucleotides described herein are directly delivered to the central nervous system (i.e., brain) of a subject in need of treatment.

CNS Delivery

Typically, direct CNS delivery or injection to the brain bypasses the blood brain barrier and delivers therapeutic agents directly to the brain tissues. Suitable CNS delivery techniques and routes include, but are not limited to, intra-parenchymal, intracerebral, intravetricular cerebral (ICV), intrathecal (e.g., IT-Lumbar, IT-cisterna magna) administrations and any other techniques and routes for injection directly or indirectly to the CNS and/or CSF.

In some embodiments, intrathecal delivery may be used according to the present invention. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

Typically, a therapeutic composition may be injected at any region surrounding the spinal canal. In some embodiments, a therapeutic composition is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level.

Blood Brain Barrier-Crossing Moieties

In some embodiments, antisense RNA oligonucleotides described herein may be modified to facilitate crossing the blood brain barrier (BBB) and/or cellular uptake into neurons. For example, antisense RNA oligonucleotides described herein may be associated with a BBB-crossing moiety. In some embodiments, a suitable BBB-crossing moiety binds to a receptor on the surface of brain cells, thereby inducing, e.g., receptor-mediated endocytosis. Exemplary BBB-crossing moieties include, but are not limited to, hormones (e.g., thyroids, steroids) and peptides (e.g., IGF-I, IGF-II, insulin, or transferrin). In some embodiments, antisense RNA oligonucleotides described herein are associated with a cell- or membrane-penetrating peptide to facilitate uptake into brain cells, such as neurons. Without wishing to be bound by theory, it is contemplated that cell- or membrane-penetrating peptides are particularly useful in facilitating cellular uptake of antisense RNA oligonucleotides into arcuate nucleus neurons, for example, proopiomelanocortin (POMC) positive neurons of the hypothalamus, which display a leaky BBB.

Exemplary cell- or membrane-penetrating peptides include, but are not limited to, HIV-TAT, Antp, penetratin, polylysine, polyarginie, VP22, Syn B1, PTD-4, Pep-1, transportan and FGF-4 peptides. See e.g., Langel, U. (ed.), "Cell-Penetrating Peptides: Processes and Applications", CRC Press, Boca Raton, Fla., 2002; Arzumanov, Abes, R., et. al., *Arginine-rich cell penetrating peptides: Design, structure-activity, and applications to alter pre-mRNA splicing by steric-block oligonucleotides,* 2008, J Pept Sci; (14): 455-60; Said, Hassane, F., *Cell penetrating peptides: overview and applications to the delivery of oligonucleotides,* 2010, Cell Mol Life Sci; (67):715-26 for further discussion and all of which are incorporated herein by reference. Suitable cell- or membrane-penetrating peptides encompass both naturally-occurring peptides and modified peptides that retain membrane penetrating ability and can be produced using recombinant and synthetic methods or purified from natural sources.

A BBB-crossing moiety including a cell- or membrane-penetrating peptide may be attached at the 5' end or 3' end of the oligo. It will be appreciated that a BBB-crossing moiety including a cell- or membrane-penetrating peptide may be associated with an antisense RNA oligo in any manner. For example, a BBB-crossing moiety (e.g., a cell- or membrane-penetrating peptide) may be chemically conjugated, or fused to an antisense RNA oligo directly or indirectly via a peptide linker or spacer. In some embodiments, a BBB-crossing moiety (e.g., a cell- or membrane-penetrating peptide) may be associated with an antisense RNA oligo via non-covalent interactions.

Inventive methods of the present invention contemplate single as well as multiple administrations of a therapeutically effective amount of antisense oligonucleotides described herein. Antisense oligonucleotides can be administered at regular intervals, depending on the nature, severity and extent of the subject's condition. In some embodiments, a therapeutically effective amount of an antisense oligonucleotide of the present invention may be administered periodically at regular intervals (e.g., once every year, once every six months, once every five months, once every three months, bimonthly (once every two months), monthly (once every month), biweekly (once every two weeks), weekly, twice a week, three times a week, daily, or twice a day).

As described above, the term "therapeutically effective amount" is largely determined based on the total amount of the therapeutic agent contained in the pharmaceutical compositions of the present invention. A therapeutically effective amount is commonly administered in a dosing regimen that may comprise multiple unit doses. For any particular composition, a therapeutically effective amount (and/or an appropriate unit dose within an effective dosing regimen) may vary, for example, depending on the desired therapeutic effects, route of administration or on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration; the duration of the treatment; and like factors as is well known in the medical arts.

In some embodiments, a therapeutically effective dose may range from about 0.005 mg/kg weight to 500 mg/kg weight, e.g., from about 0.005 mg/kg weight to 400 mg/kg weight, from about 0.005 mg/kg weight to 300 mg/kg weight, from about 0.005 mg/kg weight to 200 mg/kg weight, from about 0.005 mg/kg weight to 100 mg/kg weight, from about 0.005 mg/kg weight to 90 mg/kg weight, from about 0.005 mg/kg weight to 80 mg/kg weight, from about 0.005 mg/kg weight to 70 mg/kg weight, from about 0.005 mg/kg weight to 60 mg/kg weight, from about 0.005 mg/kg weight to 50 mg/kg weight, from about 0.005 mg/kg weight to 40 mg/kg weight, from about 0.005 mg/kg weight to 30 mg/kg weight, from about 0.005 mg/kg weight to 25 mg/kg weight, from about 0.005 mg/kg weight to 20 mg/kg weight, from about 0.005 mg/kg weight to 15 mg/kg weight, from about 0.005 mg/kg weight to 10 mg/kg weight.

In some embodiments, the therapeutically effective dose may also be defined by mg/kg brain weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 3.

TABLE 3

Dosage conversion
Correlation between Brain Weights, body weights and ages of males

| Age (year) | Brain weight (kg) | Body weight (kg) |
| --- | --- | --- |
| 3 (31-43 months) | 1.27 | 15.55 |
| 4-5 | 1.30 | 19.46 |

In some embodiments, the therapeutically effective dose may also be defined by mg/15 cc of cerebrospinal fluid (CSF). As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual in need and the professional judgment of the person administering or supervising the administration of the therapeutic agent and that dosage ranges set forth herein are exemplary only and are not intended to limit the scope or practice of the claimed invention.

Gene Therapy

In some embodiments, antisense oligonucleotides may be delivered as naked recombinant RNAs in pharmaceutical compositions through conventional administration routes described above. In some embodiments, constructs encoding an antisense oligonucleotide of interest may be delivered through gene therapy approaches. Various gene therapy vectors may be used to practice the present invention.

In some embodiments, retroviral vectors are used for expressing an antisense oligonucleotide of interest. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are typically also required for integration in the host cell genome (Coffin, 1990).

In order to construct a retroviral vector, a nucleic acid encoding a gene of interest is inserted into the viral genome in the place of certain viral sequences to produce a virus that is replication-defective. In some embodiments, in order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. Suitable retroviral based vectors include, but are not limited to, lenitvirus based vectors including various pseuodotyped lentiviral vectors. Exemplary lentiviral vectors are described in U.S. Pat. No. 5,834,256 and U.S. Pat. No. 5,716,832, the teachings of which are hereby incorporated by reference.

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. In some embodiments, adenovirus-, or adeno-associated virus based vectors (Levrero et al., 1991; Gomez-Foix et al., 1992; Stratford-Perricaudet and Perricaudet, 1991; Stratford-Perricaudet et al., 1990; Rich et al., 1993) are used. Various recombinant AAV vectors (e.g., AAV1, AAV2, AAV3, AAV4, AAV5, AAV6, AAV7, or AAV8) are available in the art and may be used to practice the invention.

Various methods may be used to deliver viral vectors encoding a gene of interest and are known in the art. For example, recombinant adeno- or adeno-associated virus based vectors may be delivered through trachea instillation (Rosenfeld et al., 1991; Rosenfeld et al., 1992), muscle injection (Ragot et al., 1993), peripheral intravenous injections (Herz and Gerard, 1993), stereotactic inoculation into the brain (Le Gal La Salle et al., 1993), and intrathecal delivery as described herein.

Kits

The present invention further provides kits or other articles of manufacture which contains a therapeutic agent of the present invention (e.g., antisense oligonucleotides), tools for administration, and/or instructions for its use. For example, kits or other articles of manufacture may include a container, an IDDD, a catheter and any other articles, devices or equipment useful in intrathecal administration and associated surgery. Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container holds formulations containing a therapeutic agent of the invention (e.g., antisense oligonucleotides) and a label on, or associated with, the container that may indicate directions for reconstitution and/or use. For example, the label may indicate that the formulation is reconstituted to concentrations as described above. The label may further indicate that the formulation is useful or intended for, for example, IT administration. In some embodiments, a container may contain a single dose of a stable formulation containing a therapeutic agent. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final concentration of a therapeutic moiety in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Example 1

Identification of Oligonucleotides that Target the HTR2C Exon V/Intron V Region by Oligo Walk As described above, the 5-HT$_{2C}$ receptor (HTR2C) plays an important role in the control of appetite and energy balance. It has been previously demonstrated that HTR2C-knockout mice develop hyperphagia and obesity. It was also reported that mice with altered HTR2C RNA editing display characteristics of Prader-Willi Syndrome (PWS). HTR2C transcripts generally undergo extensive processing in the region spanning the competing alternative splicing donor sites of exon5. HTR2C pre-mRNA forms an extensive base-paired structure that is subject to RNA editing and regulation by snoRNAs, such as psnoRNA MBII-52, which is missing in patients with PWS. It has been demonstrated that psnoRNA MBII-52 plays an important role in generating the non-edited HTR2C Vb isoform, which is the most active form of the 5-$HT_{2C}$ receptor, and it acts through inducing a change in alternative splicing. Kishore S. *Science*, (2006), 311:230-232.

Figure 2:
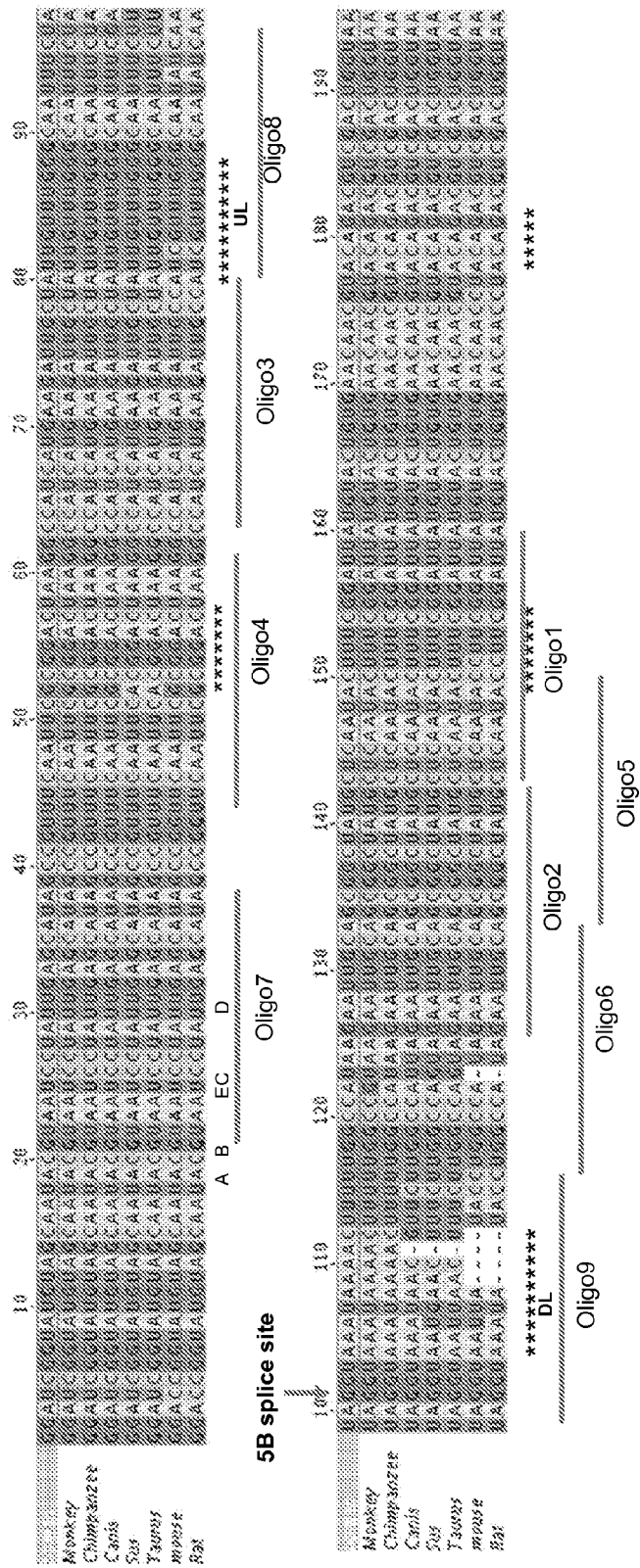
FIG. 2 illustrates exemplary sequence alignments of the Exon V/Intron V junction region of the 5'-HT2C receptor (HTR2C) from various organisms, including human (SEQ ID NO:17), monkey (SEQ ID NO:18), chimpanzee (SEQ ID NO:19), canis (SEQ ID NO:20), sus (SEQ ID NO:21), Taurus (SEQ ID NO:22), mouse (SEQ ID NO:23) and rat (SEQ ID NO:24).

This example illustrates identification of oligonucleotides that may substitute the loss of psnoRNA in PWS patients. Specifically, oligo-walking experiments were performed using short antisense RNA oligonucleotides complementary to various regions of the exon V/intron V junction of the HTR2C encompassing the psnoRNA binding region, to identify potential sites for altering HTR2C pre-mRNA splicing (FIG. 1). Sequences of the human and mouse HTR2C exon V/intron V sequence are shown in Table 4 (uppercase: exon V, lowercase: intron V). Comparison of the exon V/intron V sequence between several different organisms are shown in FIG. 2 and demonstrates a high degree of homology across different species in this region.

stability against exogenous nucleases and facilitate direct uptake by the cell. The short antisense RNA oligonucleotides tested include those listed in Table 5.

TABLE 5

Short Antisense RNA Oligonucleotides

| Oligo # | Sequence (5'-3') | SEQ ID NO: |
|---|---|---|
| 1 | UAAUCCGAAAGUAUUGAG | 1 |
| 2 | CAUAGCCGCUGCAAUUCU | 4 |
| 3 | UAGCAAUCUUCAUGAUGG | 10 |
| 4 | UUAGUCCGCGAAUUGAAA | 11 |
| 5 | AGUAUUGAGCAUAGCCGC | 5 |
| 5-5 | AGUAUUGAGCAU | 6 |
| 5-3 | GAGCAUAGCCGC | 7 |
| 6 | UGCAAUUCUUAUGGCCAA | 8 |
| 7 | AUGCUCAAUAGGAUUACG | 12 |
| 8 | AGAAAUUGCCCAAACAAU | 13 |
| 9 | AAAGUUUUAUUUACCUAU | 14 |

In vitro RNA structure assays were performed to confirm binding for each of the tested antisense oligonucleotides, to the target region within the minigene pre-mRNA structure. For the study, each antisense RNA oligonucleotide was independently mixed with minigene pre-mRNA, hybridized under stringent conditions and digested with RNase A/T1. Binding of the antisense RNA oligonucleotide to the minigene results in a change in pre-mRNA three dimensions structure and its overall sensitivity to RNase cleavage.

TABLE 4

HTR2C exon5/intron5 sequence

| | | |
|---|---|---|
| human HTR2c exonV/intronV | ATTATGTCTGGCCACTACCTAGATATTTGTGCCCCGTCTGGATTTCTTTAGATGTTT TATTTTCAACAGCGTCCATCATGCACCTCTGCGCTATATCGCTGGATCGGTATGTAG CAATACGTAATCCTATTGAGCATAGCCGTTTCAATTCGCGGACTAAGGCCATCATGA AGATTGCTATTGTTTGGGCAATTTCTATAGgtaaataaaActttttggccataagaa Ttgcagcggctatgctcaatactttcggattatgtactgtgaacaacgtacagacgt Cgactggtaa | SEQ ID NO:2 |
| mouse HTR2c exonV/intronV | ATTATGTCTGGCCTTTACCTAGATATTTGTGCCCCGTCTGGATTTCACTAGATGTGC TATTTTCAACTGCGTCCATCATGCACCTCTGCGCCATATCGCTGGACCGGTATGTAG CAATACGTAATCCTATTGAGCATAGCCGGTTCAATTCGCGGACTAAGGCCATCATGA AGATTGCCATCGTTTGGGCAATATCAATAGgtaattatacctggccatagaatTgca Gcggctatgctcaatacctteggattatgtactgtgaacaacctacagacgtcgact Ggtaa | SEQ ID NO:3 |

Figure 3:
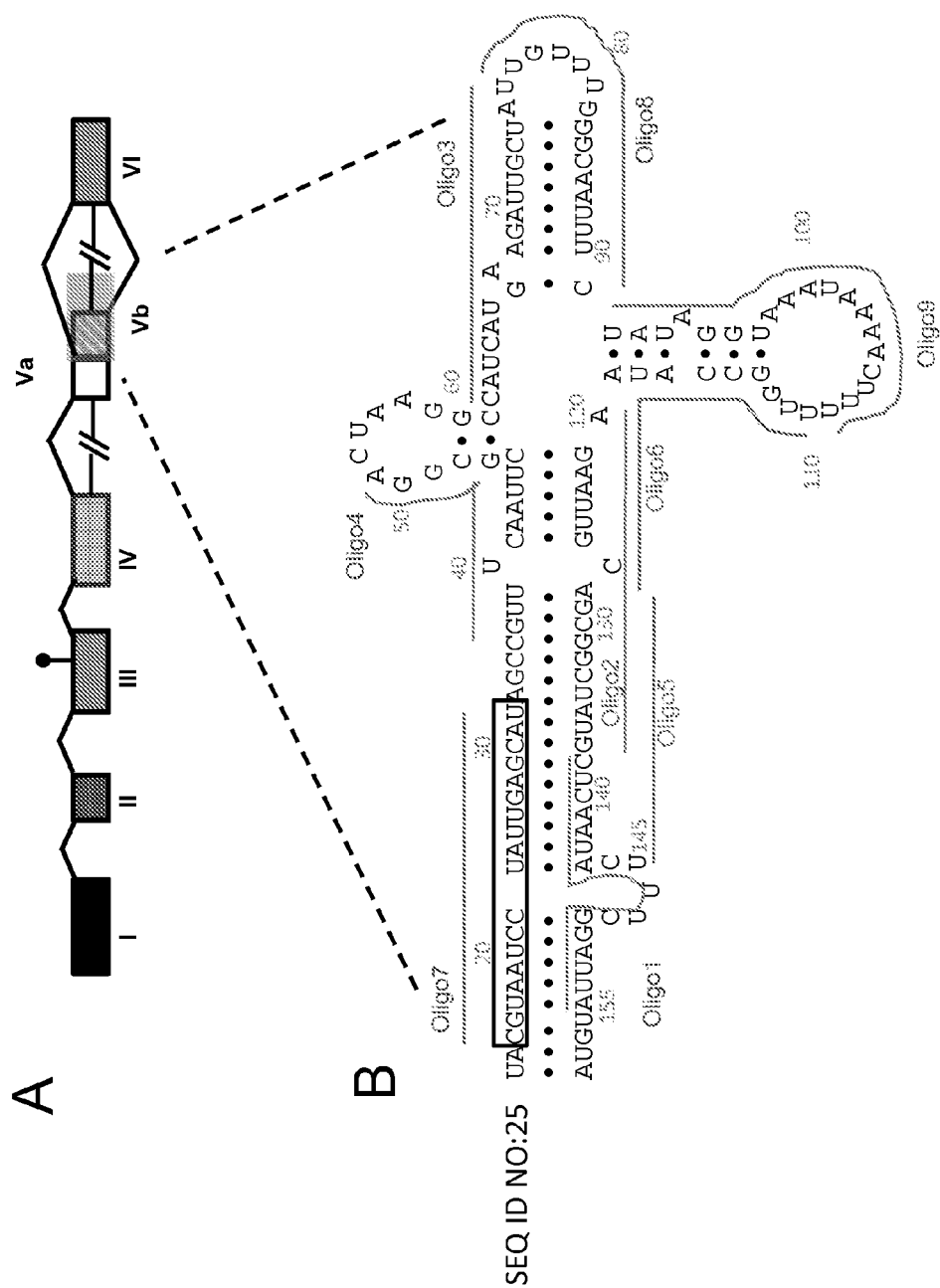
FIG. 3 (A) illustrates the structure of an exemplary HTR2C minigene containing the alternative Exon Vb region. (B) illustrates the sequence of the shaded area within the minigene diagram shown in (A), which corresponds to the Exon V/Intron V region. The psnoRNA complementary region is shown as framed sequence. Also depicted are the target regions of oligos 1-9.
Figure 4:
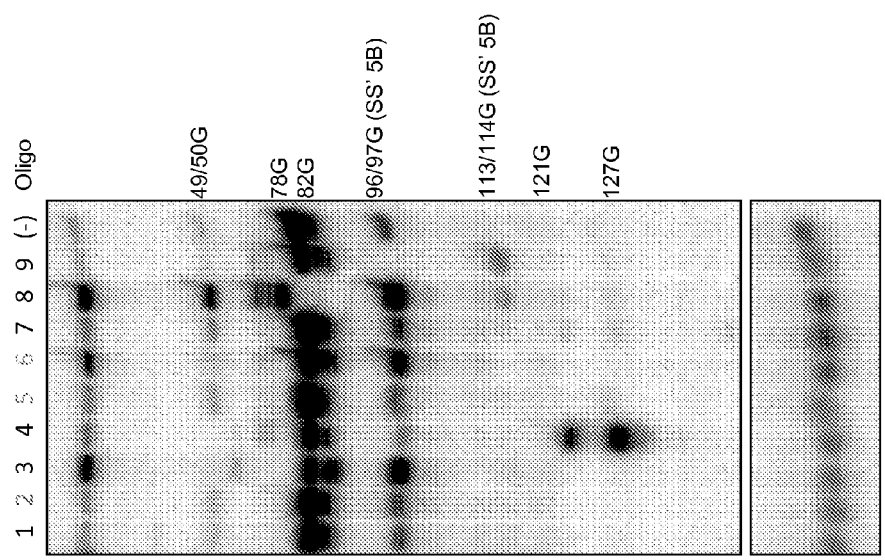
FIG. 4 depicts exemplary results from an RNA binding assay with oligos 1-9.

Panel A of FIG. 3 depicts the structure of the human HTR2C reporter minigene (minigene) used for the oligo walk experiment. The minigene encompasses exon V which contains the alternative exon Vb region. The shaded area within the minigene diagram corresponds to the sequence shown in panel B. Several important elements are located within the exon V/intron V region, such as the snoRNA complementary region (framed sequence in FIG. 3B). The minigene was constructed as described previously (O. Stoss et. al., *Brain Research Protocols*; (4), 383; 1999). Briefly, the minigene was constructed using 3'-end sequence regions of exon V (approximately 100 nt in length) and the 5' end of intron V (approximately 97 nucleotides in length) from the human serotonin receptor 2C gene. The sequences were amplified from HEK293 genomic DNA via PCR amplification, ligated and subcloned into the pCRII vector (Invitrogen®) under the control of a SP6 promoter sequence. Each of the various short antisense RNA oligonucleotides tested in the oligo walk experiments are shown in FIG. 3B, along with their corresponding binding sites on the HTR2C pre-mRNA sequence. All of the short antisense RNA oligonucleotides were synthesized as 2'-O-methyl thioates, to enhance Following treatment, RNA was recovered and analyzed on a denaturing polyacrylamide gel. FIG. 4 shows exemplary results indicating that each of antisense RNA oligos 1-9 bind to the HTR2C pre-mRNA minigene (FIG. 4).

Example 2

Oligo 5 and Other Oligonucleotides Promote Exon Vb Inclusion

This example demonstrates that certain short antisense RNA oligonucleotides that bind to specific regions within the exon V/intron V junction of pre-mRNA sequence can alter splicing and promote exon Vb inclusion, resulting in generation of the HTR2C Vb isoform.

Figure 5:
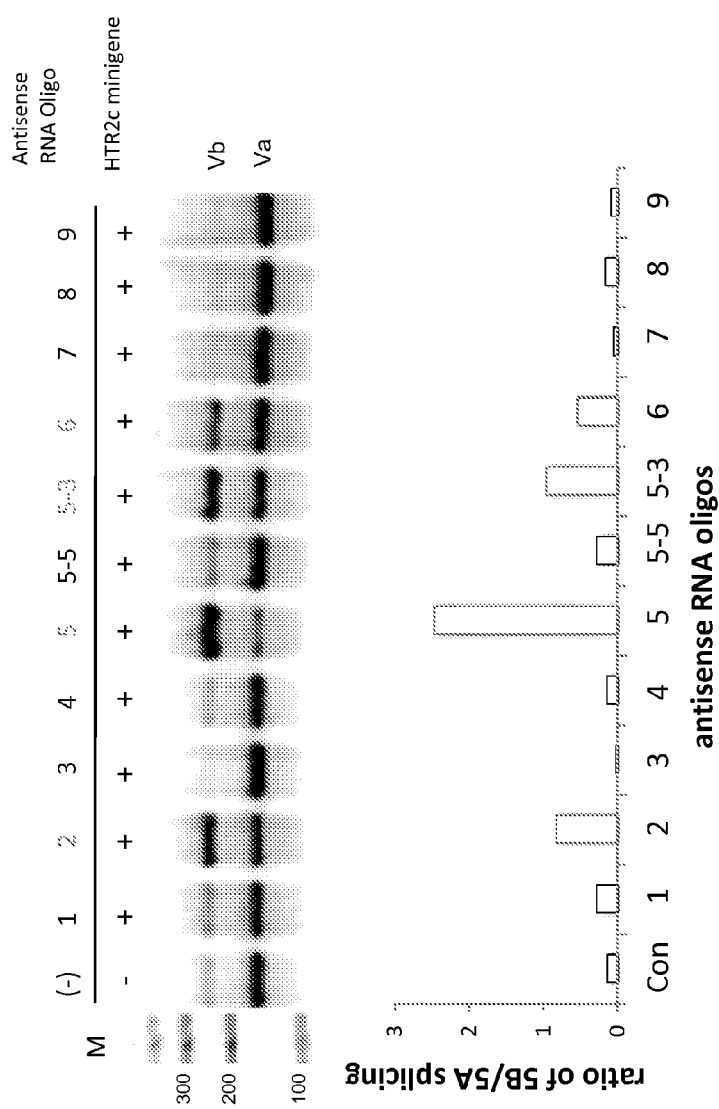
FIG. 5 depicts exemplary results showing effects of oligonucleotides 1-9 in modulating the expression of HTR2C Vb vs. Va isoforms. 1 μg of each oligonucleotide was added to HEK293 cells transfected with the reporter gene shown in FIG. 3. Detection was by RT-PCR. The quantification shown in the lower panel is the average of three experiments.

For each experiment, HEK293 cells were transiently co-transfected, using a calcium phosphate precipitation method, with the HTR2C minigene plasmid, an antisense RNA oligo and a GFP expression vector (to visually monitor the rate of transfection). Specifically, HEK cells were cultured in DMEM containing 10% (v/v) fetal bovine serum (Invitrogen). RNA oligonucleotides and plasmid DNAs were transfected into cells with calcium phosphate. Typically, 50 ng of RNA nucleotide and 100 ng of DNA plasmid were transfected into $1\times10^6$ cells. Serotonin receptor 2C gene splicing analysis was performed as described in Kishore S. *Science*, (2006), 311:230-232. Briefly, total RNA was isolated 17-24 hours post transfection, subjected to RT-PCR using each antisense RNA oligonucleotide as a primer and the reaction product analyzed on a 2% agarose TBE gel (FIG. 5). The data show that antisense RNA oligonucleotides including oligo #5, and to a lesser extent oligo #2, and oligo #6, promoted exon Vb inclusion and led to generation of the HTR2C Vb splice isoform according to predicted band size (FIG. 5).

Figure 6:
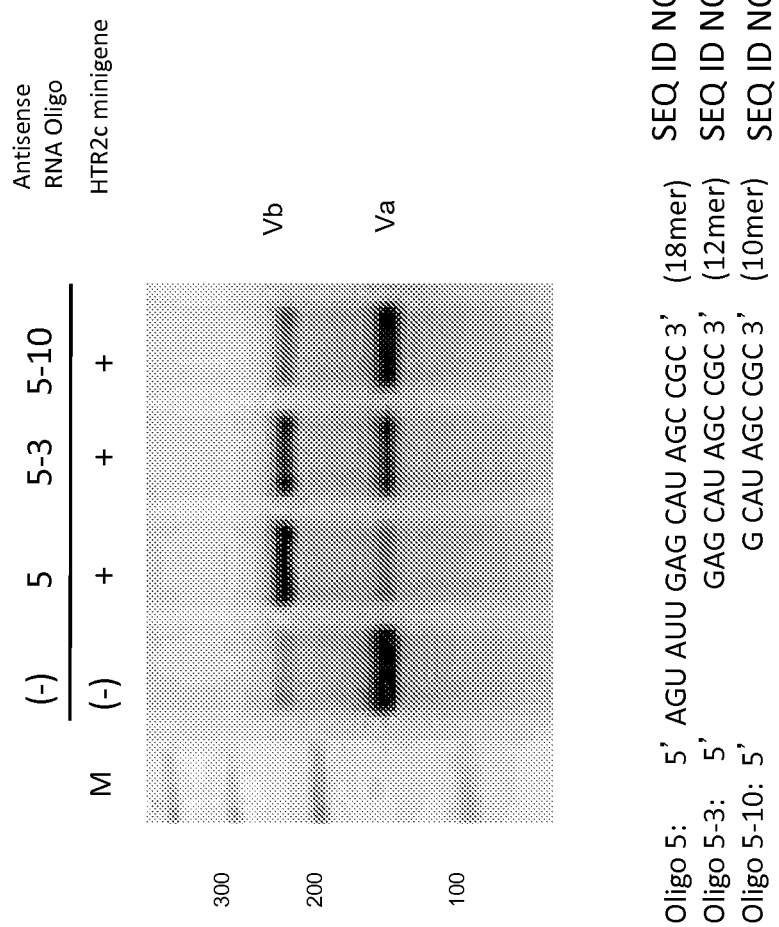
FIG. 6 illustrates exemplary results showing effects of certain shortened versions of oligo #5 in modulating the expression of HTR2C Vb vs. Va isoforms.

As shown in FIG. 5, oligo #5 had the strongest effect on splice site selection promoting exon Vb inclusion. Further experiments were performed using shortened versions of oligo #5, such as oligos #5-3 (GAGCAUAGCCGC), #5-5 (AGUAUUGAGCAU), and #5-10 (GCAUAGCCGC), to examine if smaller regions within the foot print of oligo #5 could be used to elicit the similar effect as the full length 18 mer. Exemplary results are shown in FIGS. 5 and 6. As can be seen, these shortened oligonucleotides showed a smaller effect on exon inclusion than the full-length oligo #5.

Figure 7:
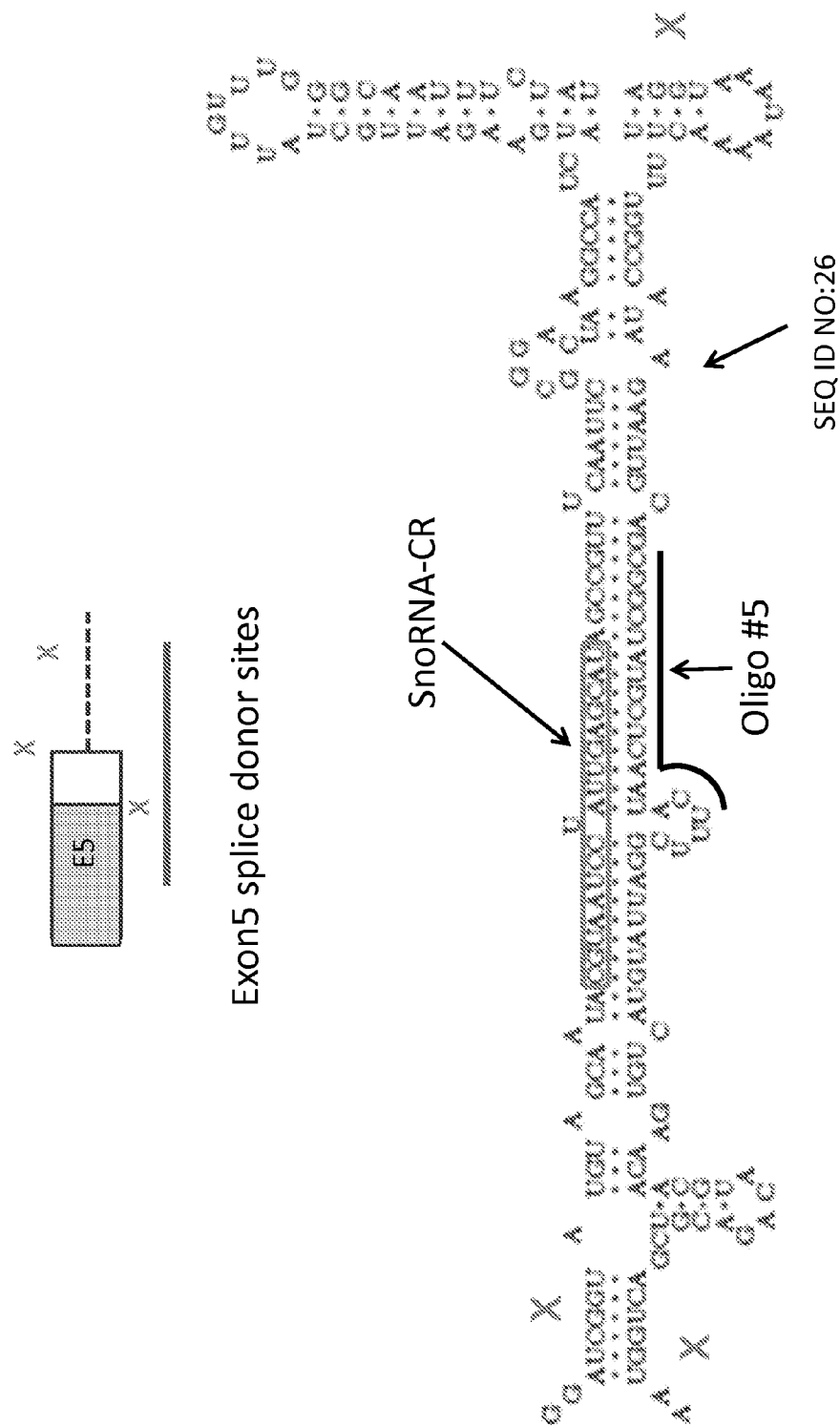
FIG. 7 illustrates that oligo #5 and psnoRNA HBII-52 may target the same secondary structure of the Exon 5/Intron 5 region of HTR2C pre-mRNA. Three known splice donor sites are shown as X. The psnoRNA complementary region is shown as framed sequence.

As shown in FIG. 3, the oligos #2, #5 and #6 all bind to intron V region that forms a stem structure with exon Vb. Evolutionary, this region is highly conserved, showing only one U38>G substitution in mouse and rat that will interfere with the stem, but a total of three C35>U and G129>A substitutions in naked mole and microbat that keep the stem structure. For example, the binding site of oligo #5 overlaps with about half of the psnoRNA binding site (framed sequence in FIG. 3) located on the complementary RNA strand of exon Vb. Without wishing to be bound by theory, it is contemplated that both the psonRNA and oligo #5 target the same secondary structure on the HTR2C (FIG. 7).

Example 3

Oligo #5 is Effective in the Nanomolar Range

Oligo #5 is selected as an exemplary oligonucleotide of the present invention for further studies. In this example, we used the full length oligo #5 to determine its efficacy in cell culture and demonstrated that oligo #5 works in the nanomolar range.

Figure 8:
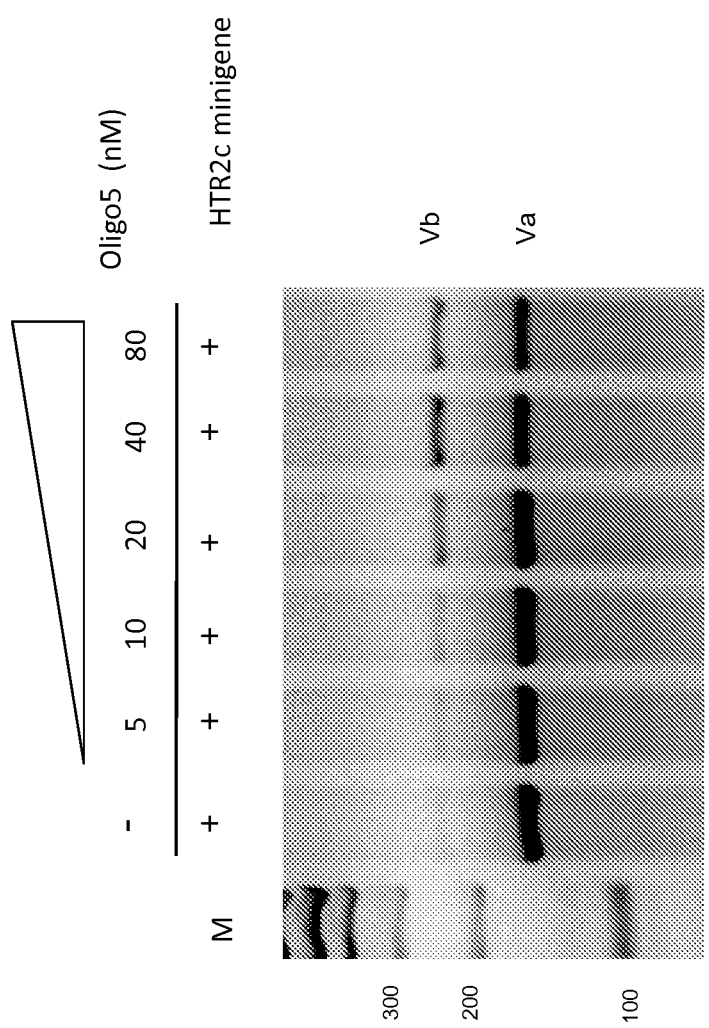
FIG. 8 depicts exemplary dose-response results showing effects on HTR2C isoform generation after treating cells with varying concentrations of oligo #5.

Specifically, oligo #5 and a reporter minigene were transfected into HEK293 cells as described above. Oligo #5 was added without transfection reagent to the cells that take up phosphor-thio RNAs. As shown in FIG. 8, the oligo starts showing an effect in driving the expression of the 5-HTR2C Vb isoform at 5 nM and the effect is strongest in the 40 nM range.

Figure 9:
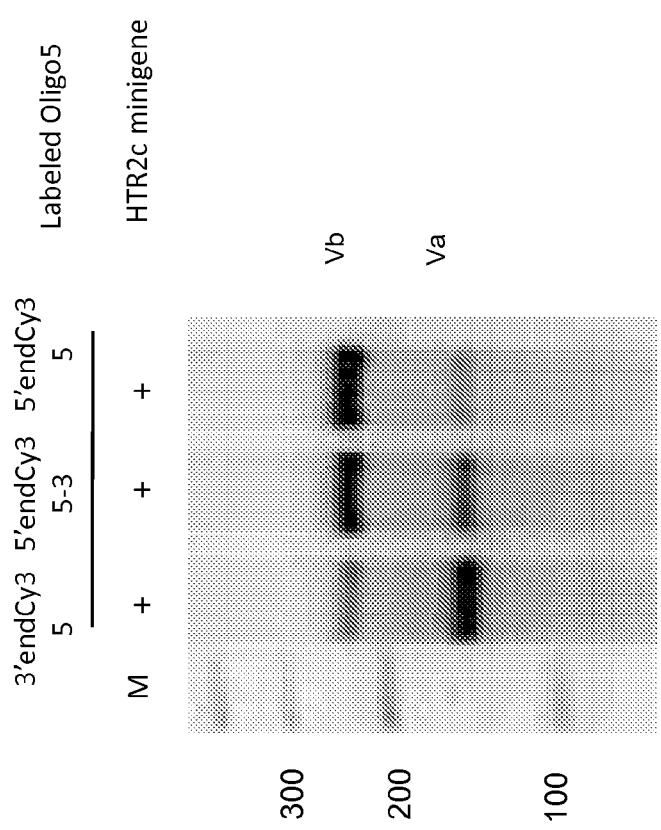
FIG. 9 depicts exemplary results showing the effects on HTR2C isoform generation after treating cells with 3' end or 5' end Cy3-modified oligo #5.
Figure 10:
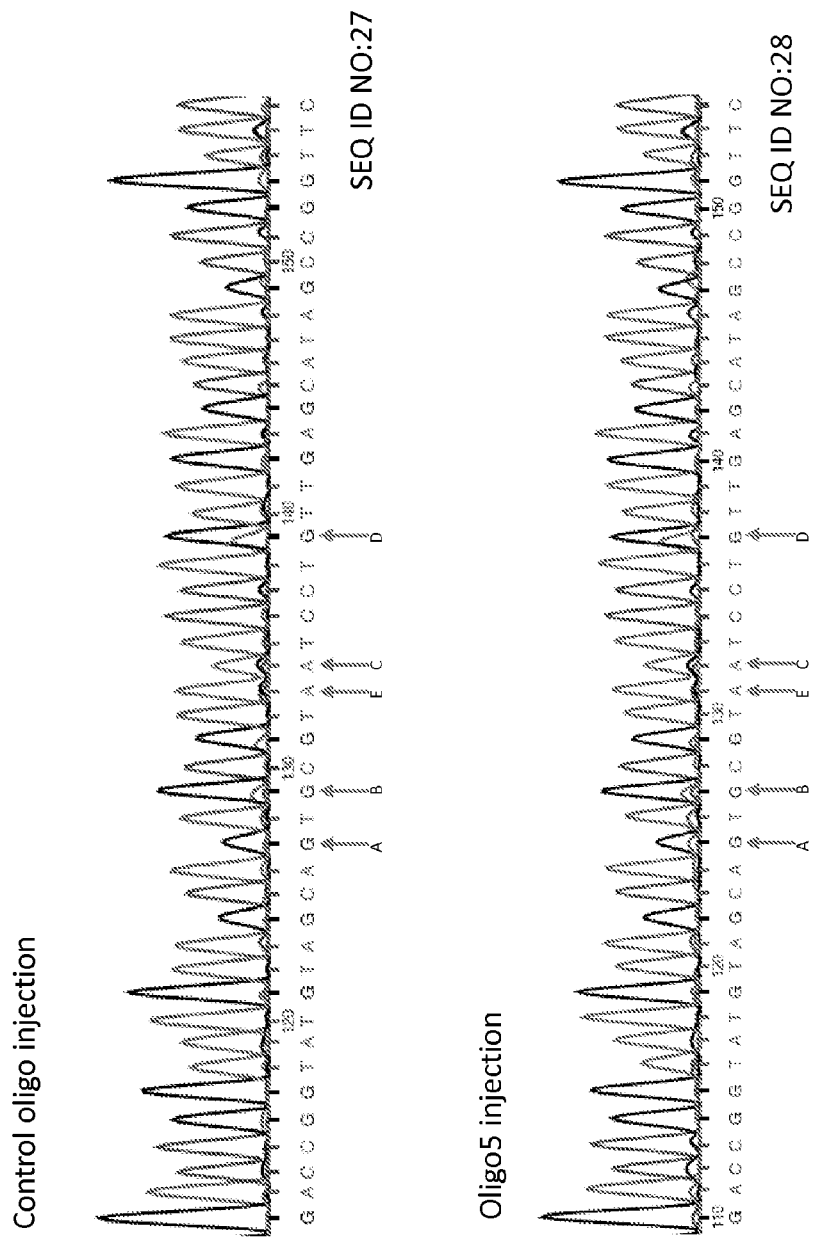
FIG. 10 illustrates exemplary results from direct sequencing of the exon inclusion band generated following treatment with oligo #5.

To follow the oligonucleotide in cells, we labeled either the 5' or 3' end with Cy3. All oligos are taken up by the cell and accumulate in the nucleus, as expected. As shown in FIG. 10, the 5' modification does not affect the effectiveness of oligo #5. However, in this particular experiment, the 3' end modification with Cy3 reduces its effectiveness (FIG. 9). Cy3 is attached to the last base of the oligo.

Since psnoRNA promotes exon Vb inclusion through RNA editing which involves enzymatic modification, we determined if oligo #5 acts similarly through directly modulating editing. To that end, we directly sequenced the exon inclusion band caused by oligo #5 and, as shown in FIG. 10, we did not observe evidence for editing, suggesting that oligo #5 acts directly on the RNA, without inducing an enzymatic modification.

Example 4

Oligo 5 is Successfully Delivered to Neurons of Hypothalamus In Vivo

This example demonstrates that oligo 5, once injected to the brain, can be successfully delivered to the neurons of hypothalamus.

We injected 2 µg Cy3-labeled oligo #5 stereotactically into the third ventricle of naïve BL6 mice. Specifically, 9-12 week old adult male naïve C57BL/6 mice were stereotaxically implanted with a guide cannula to the coordinates of 0.83 mm posterior to the bregma, 4.0 mm below the surface of the skull, and 0.0 mm lateral to midline. The cannula tip was located above the 3rd ventricle. After the surgery, the mice were individually housed and deprived of food with continuous water supply. The injection was performed 24 hours after cannula implant. An injector with 1.0 mm projection (Plastics One) was inserted through the guide cannula and used to inject 2 ul of RNA nucleotides during at least 2 minutes. Food was resumed after the injection. The body mass and food intake were recorded at the designated time points. No seizures were detected in any of the mice, following injection of oligo #5.

Figure 11:
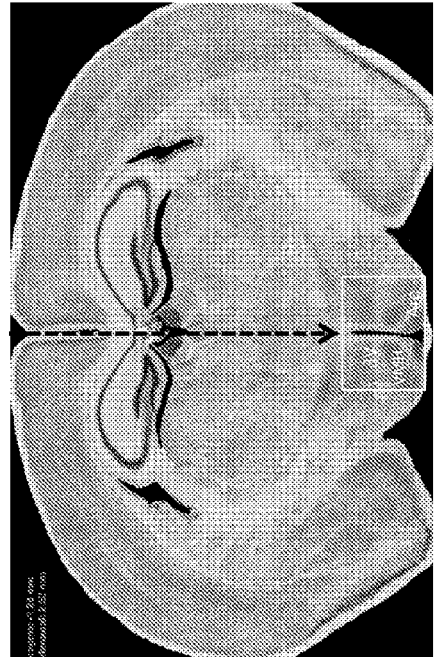
FIG. 11 (A) depicts a stereotactical view of a mouse cranial injection site. (B) depicts an exemplary fluorescence microscopy image of the $3^{rd}$ ventrical region in a mouse brain following injection of Cy3-labeled oligo #5.
Figure 11:
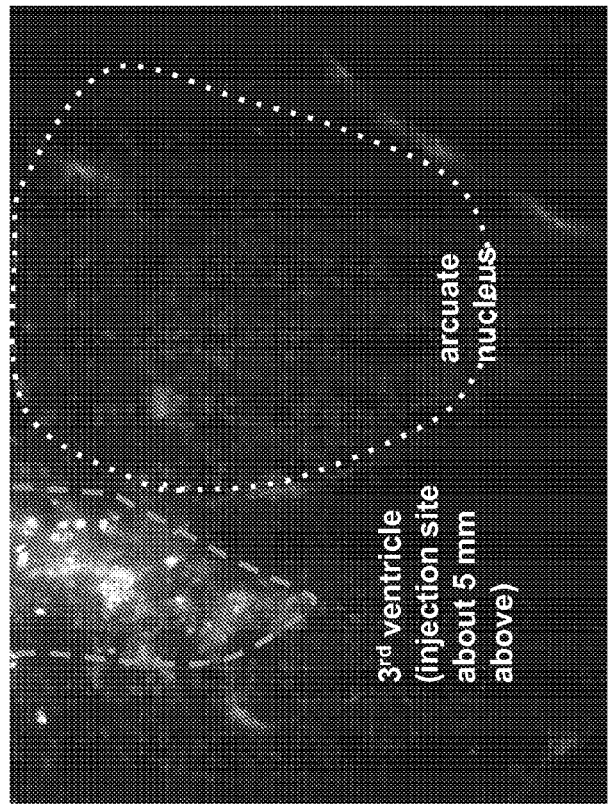
Figure 12:
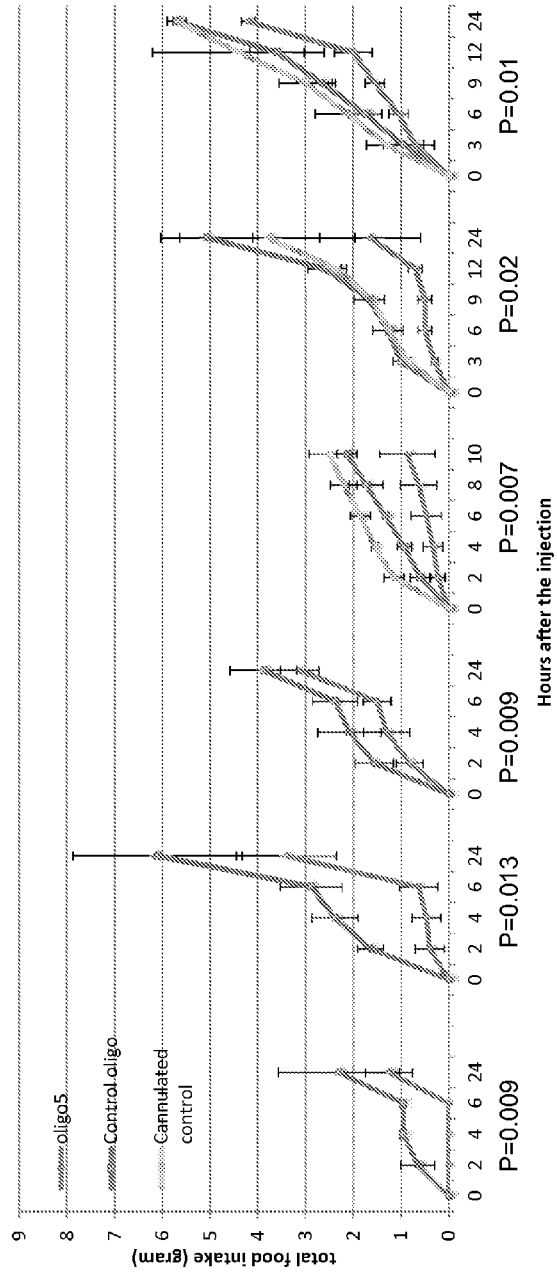
FIG. 12 depicts exemplary results showing the total food intake for mice over various time points following injection with either oligo #5, control oligo or no treatment (cannulated control).

Approximately 18 hours after injection, each mouse was sacrificed, and the brain tissue was harvested for analysis. As shown in FIG. 12, 18 hours post injection, fluorescence was detected in the nuclei of the arcuate nucleus, which consists mainly of neurons, including preopiomelanocortin positive neurons expressing the 5-HTR2C (FIG. 11). These results demonstrate that oligo #5 are successfully delivered to the nucleus of the neurons in the hypothalamus following injection to the brain.

Example 5

Oligo #5 Reduces Food Intake in Mice

As described in Examples 2 and 3, in vitro, oligo #5 increased the abundance of the non-edited version of the HTR2C. Therefore, oligo #5 acts like a genetic agonist for the serotonin receptor 2C. In this example, we further demonstrated that oligo #5 causes an anorexic response in vivo by measuring the food intake after oligo #5 injection.

As described above, 9-12 week old adult male naïve C57BL/6 mice were stereotaxically implanted with a guide cannula to the coordinates of 0.83 mm posterior to the bregma, 4.0 mm below the surface of the skull, and 0.0 mm lateral to midline. The mice were randomly divided into three study groups, individually housed, deprived of food and given a continuous supply of water. Approximately 24 hours post surgery, an injector with a 1.0 mm projection was inserted through the guide cannula and used to inject 4 µl of either oligo #5 or control oligo against human SMN2 at 1 nmol (~8 µg). The third group was injected nothing (cannulated control). Food was resumed immediately following the injection. Total body mass (data not shown) and food intake was recorded at various time points. As shown in FIG. 12, mice injected with oligo #5 showed a significant reduction in food intake for at least eight hours post the injection compared to both the control oligo and cannulated control mice.

Figure 13:
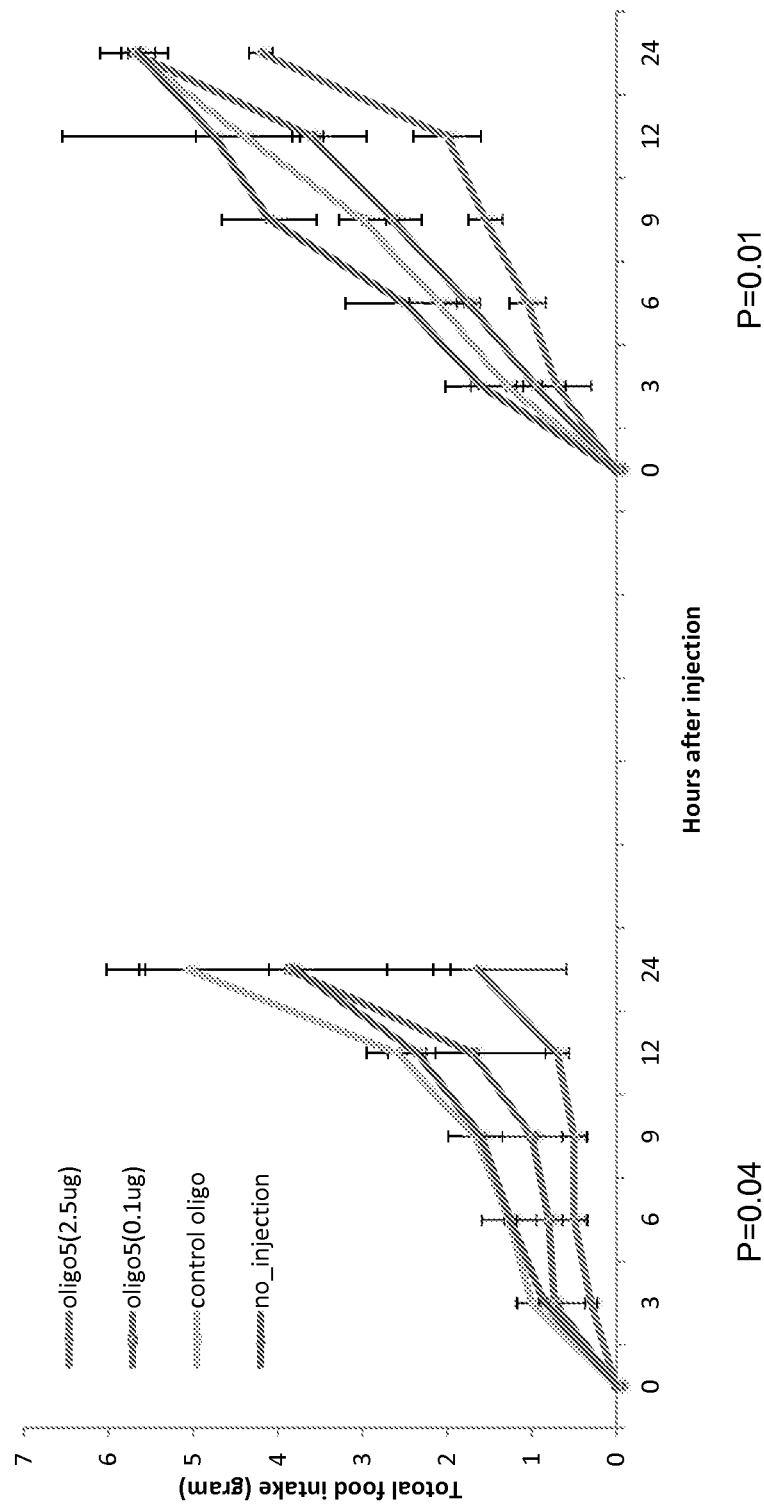
FIG. 13 illustrates exemplary results demonstrating that oligo #5 reduces food intake in a dose dependent manner.

We then tested if oligo #5 acts in a dose dependent manner. 9-12 week old adult male naïve C57BL/6 mice were cannulated, divided up into four study groups and maintained as described above. Approximately 24 hours post surgery, the mice received either no injection, control oligo, 0.1 µg of oligo #5, or 2.5 µg of oligo #5. Food was resumed immediately following the injection. Total body mass (data not shown) and food intake was recorded at various time points over a 2 day period. As shown in FIG. 13, oligo #5 reduces food intake in a dose dependent manner. However, even the lower dose, 0.1 µg (20 pmol) of oligo #5, shows an effect in reduction of food intake by mice.

Taken together, injection of oligo #5 to the brain effectively inhibits or reduces animal food consumption, indicating that oligo #5, and other similar oligonucleotides, can be used to treat hyperphagia in PWS patients.

Example 6

Exemplary Model

As described above, our data demonstrate that small antisense RNA oligonucleotides 1-9 are able to bind to different regions within the HTR2C pre-mRNA structure, and some are capable of inducing changes in its three dimensional conformation. Our data also suggest small antisense oligo #5, which overlaps with approximately half of the snoRNA binding site located on the complementary RNA strand in exon Vb (FIG. 7), is able to promote exon Vb inclusion in vitro to produce the HTR2C Vb isoform (FIG. 5). In vivo experiments demonstrate that injection of oligo #5 into the brain is directly taken up into the cell and dramatically reduces food intake by mice. Furthermore, injection of oligo #5 is able to promote an anorexic state in a dependent response.

Figure 14:
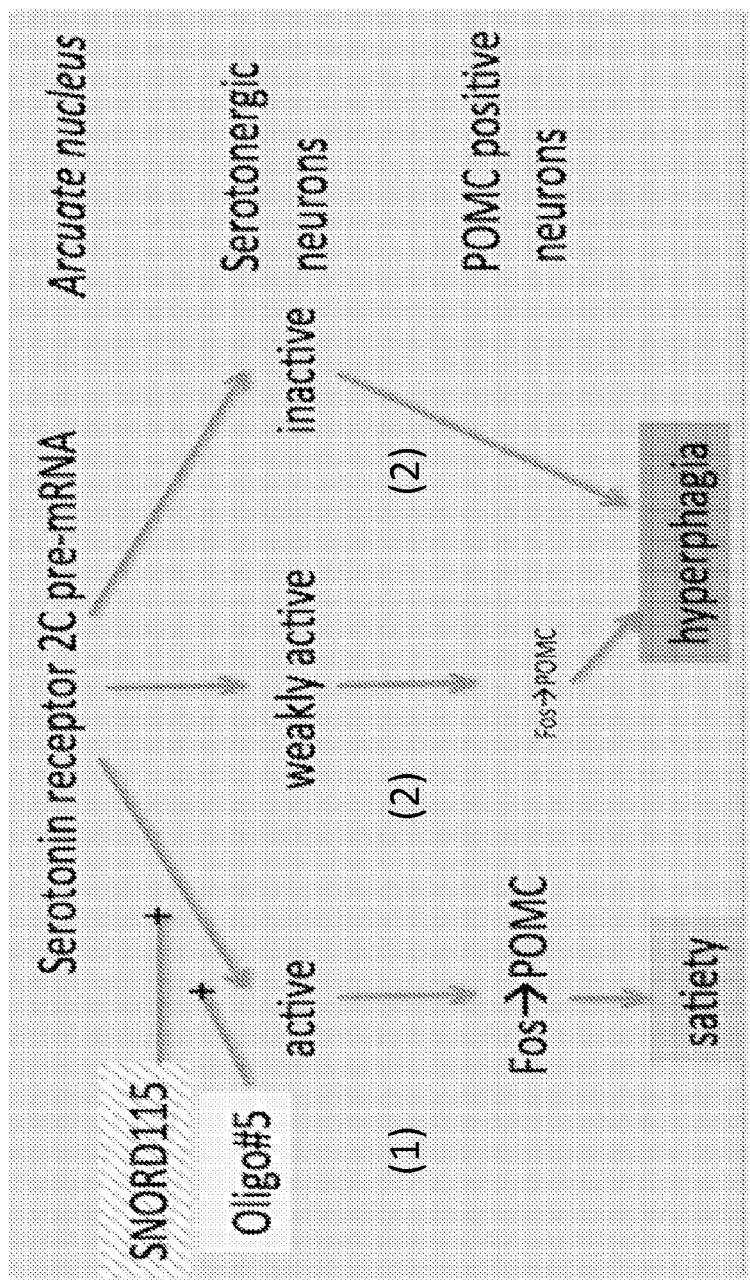
FIG. 14 depicts an exemplary working model for 5'-HT2C receptor (HTR2C) Vb isoform signaling.

Previous studies have demonstrated that activation of the regulated splice site within this region of the 5-HTR2C pre-mRNA needs to be activated to generate the 5-HTR2C Vb isoform, which is the most active form of the receptor (Kishore et. al., *Science*, (311), 230; 2005). In humans, this is physiologically achieved through binding of psnoRNAs to the snoRNA-CR to alter the pre-mRNA secondary structure. This is supported by the findings that patients diagnosed with PWS, fail to produce psnoRNAs or the resulting active Vb isoform; leading to a state of chronic hyperphagia. This suggests that both the psnoRNA and oligo #5 may target the same secondary structure on the HTR2C pre-mRNA to produce the active Vb isoform (FIG. 14).

Based on these data, and without wishing to be bound by any particular theory, we propose that small antisense RNA oligonucleotides, for example, oligo #5, can be used as a genetic agonist to promote generation of the active HTR2C Vb active isoform. As illustrated in FIG. 14, activation of the HTR2C receptor in POMC positive neurons quickly increases the transcription factor c-fos that turns on POMC in the arcuate nucleus. Once active, the POMC peptide is enzymatically processed into several small peptides such as alpha, beta and gamma melanocyte stimulating hormone (MSH). MSH peptides turn on the MC3/4R receptors in the paraventricular nucleus, which generate an anorexic signal. The same receptors inhibit the activity in the LHA (lateral hypothalamus), which blocks an orexic signal. As a result, the mice stop eating. Conversely, a subject who predominantly expresses the weakly active Vb or inactive Va isoform, such as in the case of a PWS patient, fails to generate sufficient c-fos activation to leave a chronic state of hyperphagia. Without wishing to be bound by any particular theory, it is contemplated that injection of oligo #5 activates c-fos, which triggers this "natural" cascade, thereby treating hyperphagia and other related symptoms in PWS and other diseases, disorders or conditions.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. An antisense oligonucleotide of 16-50 nucleotides in length comprising a sequence that permits specific hybridization to a target region of a human 5'-HT2C receptor (HTR2C) pre-mRNA under stringent conditions, wherein: the target region comprises a nucleotide sequence 5' UUG-GCCAUAAGAAUUGCAGCGGCUAUGCUCAAUACU 3' (SEQ ID NO: 1) and;
  the antisense oligonucleotide comprises a sequence at least 95% identical to 18 or more contiguous nucleotides that appear in:
  5' AGUAUUGAGCAUAGCCGCUGCAAUUC-UUAUGGCCAA 3' (SEQ ID NO: 15)
  and the antisense oligonucleotide comprises a ribose group modified with a methyl group;
  further wherein the antisense oligonucleotide, once administered to a cell, modulates 5'HT2C receptor (HTR2C) activity.

2. The antisense oligonucleotide of claim 1, wherein the sequence permits specific hybridization to nucleotides 1-18 of SEQ ID NO: 1.

3. The antisense oligonucleotide of claim 1, wherein the sequence permits specific hybridization to nucleotides 10-27 of SEQ ID NO: 1.

4. The antisense oligonucleotide of claim 1, wherein the sequence permits specific hybridization to nucleotides 19-36 of SEQ ID NO: 1.

5. The antisense oligonucleotide of claim 1, wherein the sequence permits specific hybridization to nucleotides 19-30 of SEQ ID NO: 1.

6. The antisense oligonucleotide of claim 1, wherein the sequence is at least 90% identical to any of 5' UGCAAUUC-UUAUGGCCAA 3' (SEQ ID NO:8), 5' CAUAGCCGCUG-CAAUUCU 3' (SEQ ID NO:4), 5' AGUAUUGAG-CAUAGCCGC 3' (SEQ ID NO:5), or 5' GAGCAUAGCCGC 3' (SEQ ID NO:7).

7. A pharmaceutical composition comprising the antisense oligonucleotide of claim 1, and a pharmaceutically acceptable carrier.

8. A kit comprising an antisense oligonucleotide of claim 1; and tools for administration to the brain of a mammal.

9. The antisense oligonucleotide of claim 1, wherein the antisense oligonucleotide comprises a ribose group modified with a 2' O-methyl group.

10. The antisense oligonucleotide of claim 1, wherein the antisense oligonucleotide comprises one or more phosphorothioate linkages between ribose groups.

11. An antisense oligonucleotide, no more than 50 nucleotides long, comprising a sequence that permits specific hybridization to a target region of a human 5'-HT2C receptor (HTR2C) pre-mRNA under stringent conditions, wherein:
   the target region comprises a nucleotide sequence 5' UUGGCCAUAAGAAUUGCAGCGGCUAUGCUCAAUACU 3' (SEQ ID NO: 1);
   the antisense oligonucleotide is selected from the group consisting of 5' UGCAAUUCUUAUGGCCAA 3' (SEQ ID NO: 8), 5' CAUAGCCGCUGCAAUUCU 3' (SEQ ID NO:4), 5' AGUAUUGAGCAUAGCCGC 3' (SEQ ID NO:5), and 5' GAGCAUAGCCGC 3' (SEQ ID NO:7);
   the antisense oligonucleotide comprises a ribose group modified with a methyl group;
   and further wherein the antisense oligonucleotide, once administered to a cell, modulates 5'HT2C receptor (HTR2C) activity.

12. A method of modulating human 5'-HT2C receptor (HTR2C) activity in a cell, the method comprising delivering an antisense oligonucleotide of claim 1 to the cell.

13. The method of claim 12, wherein the cell is a neuron.

14. The method of claim 13, wherein the neuron is in the hypothalamus region of the brain.

15. The method of claim 14, wherein the antisense oligonucleotide is administered at a concentration greater than 5 nM.

16. A method of reducing food consumption in a subject comprising administering to a subject in need of treatment an antisense oligonucleotide of claim 1.

17. A method of treating hyperphagia comprising administering to a subject in need of treatment an antisense oligonucleotide of claim 1.

18. A method of treating obesity comprising administering to a subject in need of treatment an antisense oligonucleotide of claim 1.

19. A method of treating Prader-Willi syndrome comprising administering to a subject in need of treatment an antisense oligonucleotide of claim 1.

* * * * *